United States Patent
Alami et al.

(10) Patent No.: US 10,653,694 B2
(45) Date of Patent: May 19, 2020

(54) CYTOTOXIC COMPOUNDS WHICH ARE INHIBITORS OF THE POLYMERISATION OF TUBULIN

(71) Applicants: CENTRE NATIONAL DE LA RECHERCHE SCIENTIFIQUE (CNRS), Paris (FR); UNIVERSITE PARIS-SUD, Orsay (FR)

(72) Inventors: Mouad Alami, Bussy Saint Georges (FR); Jean-Daniel Brion, Saint Leu la Foret (FR); Samir Messaoudi, Chilly Mazarin (FR); Olivier Provot, Sartrouville (FR); Mohamed-Ali Soussi, Arian (TN); Jerome Bignon, Le Val Saint Germain (FR); Joelle Dubois, Gometz-la-Ville (FR); Joanna Bakala-Wdzieczak, Paris (FR)

(73) Assignees: CENTRE NATIONAL DE LA RECHERCHE SCIENTIFIQUE (CNRS), Paris (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 15/303,157

(22) PCT Filed: Apr. 9, 2015

(86) PCT No.: PCT/EP2015/057650
§ 371 (c)(1),
(2) Date: Oct. 10, 2016

(87) PCT Pub. No.: WO2015/155262
PCT Pub. Date: Oct. 15, 2015

(65) Prior Publication Data
US 2017/0035761 A1 Feb. 9, 2017

(30) Foreign Application Priority Data
Apr. 9, 2014 (FR) .................................. 14 53142

(51) Int. Cl.
| | | |
|---|---|---|
| *C07D 403/06* | (2006.01) | |
| *A61K 31/517* | (2006.01) | |
| *C07D 235/02* | (2006.01) | |
| *A61K 47/68* | (2017.01) | |
| *A61K 31/47* | (2006.01) | |
| *A61K 31/472* | (2006.01) | |
| *A61K 45/06* | (2006.01) | |
| *C07D 215/14* | (2006.01) | |
| *C07D 215/18* | (2006.01) | |
| *C07D 217/02* | (2006.01) | |
| *C07D 239/74* | (2006.01) | |
| *C07D 239/78* | (2006.01) | |

(52) U.S. Cl.
CPC ............ *A61K 31/517* (2013.01); *A61K 31/47* (2013.01); *A61K 31/472* (2013.01); *A61K 45/06* (2013.01); *A61K 47/6803* (2017.08); *C07D 215/14* (2013.01); *C07D 215/18* (2013.01); *C07D 217/02* (2013.01); *C07D 235/02* (2013.01); *C07D 239/74* (2013.01); *C07D 239/78* (2013.01); *C07D 403/06* (2013.01)

(58) Field of Classification Search
CPC .................................................. A61K 31/517
See application file for complete search history.

(56) References Cited

U.S. PATENT DOCUMENTS

| 6,103,728 A | 8/2000 | Tang et al. |
| 2011/0275643 A1 | 11/2011 | Liou et al. |

FOREIGN PATENT DOCUMENTS

| WO | WO 2006/074187 A2 | 7/2006 |
| WO | WO 2008/122620 A1 | 10/2008 |
| WO | WO 2009/147217 A1 | 12/2009 |

OTHER PUBLICATIONS

Wang et al., Tet. Let, 41(2000) 4865-4869.*
Vippagunta et al. (2001).*
Prat et al., Tel. Let, 42(2001), 4515-4518.*
Iwasa et al., (Bioorganic & Medicinal Chemistry 9 (2000) 2871-2884.*
Schubert et al., J'nal of Chem Soc. vol. 102 (1980) 5523-5528.*
McMahon et a. (2000).*
"Cancer Drug Design and Discovery" Neidle, Stephen, ed. (Elsevier/Academic Press, 2008) pp. 427-431.*
Pinedo et al. (2000).*
McMahon et al. (2000).*
Barron et al., "A fluorescence-based high-throughput assay for antimicrotubule drugs," Analytical Biochemistry, vol. 315, pp. 49-56, 2003.
Mc Gown et al., "Differential cytotoxicity of Combretastatins Al and A4 in two daunourubicin-resistant P388 cell lines," Cancer Chemother. Pharmacol., vol. 26, pp. 79-81, 1990.
Dark et al., "Combretastatin A-4, an Agent That Displays Potent and Selective Toxicity toward Tumor Vasculature," Cancer Research, vol. 57, pp. 1829-1874, May 15, 1997.
Hamze et al., "Synthesis, Biological Evaluation of 1,1-Diarylethylenes as a Novel Class of Antimitotic Agents," ChemMedChem, vol. 4, pp. 1912-1924, 2009.
Soussi et al., "The Metabolic Fate of isoCombretastatin A-4 in Human Liver Microsomes: Identification, Synthesis and Biological Evaluation of Matabolites," ChemMedChem, vol. 6, pp. 1781-1788, 2011.
Messaoudi et al., "Isocombretastatins A versus Combretastatins A: The forgotten isoCA-4 Isomer as a Highly Promising Cytotoxic and Antitubulin Agent," J. Med. Chem., vol. 52, pp. 4358-4542, 2009.
Gaskin et al., "Turbidimetric Studies of the in Vitro Assembly and Disassembly of Porcine Neurotubules," J. Mol. Biol., vol. 89, pp. 737-758, 1974.

(Continued)

*Primary Examiner* — Paul V Ward
(74) *Attorney, Agent, or Firm* — Sunit Talapatra; Foley & Lardner LLP

(57) ABSTRACT

The invention relates to compounds which are inhibitors of the polymerization of tubulin, to the methods for the production thereof, and to the uses of same.

16 Claims, No Drawings

(56) References Cited

OTHER PUBLICATIONS

Pettit et al.. "Isolation, Structure, and Synthesis fo Combretastatins A-1 and B-1, Potent New Inhibitors of Microtubule Assembly, Derived from *Combretum caffrum*," Journal of Natural Products, vol. 50, No. 1, pp. 119-131, Jan.-Feb. 1987.

Schubert et al., "Kinetic Energy Release and Position of Transition State during Intramolecular Aromatic Substitution in Ionized 1-Phenyl-1-(2-pyridyl)ethylenes," J. Am. Chem. Soc., vol. 102, pp. 5323-5328, 1980.

Yamamoto et al., "Cobalt-Catalyzed C-4 Selective Alkylation of Quinolines," Advanced Synthesis & Catalysts, vol. 356, pp. 401-405, 2014.

Maity et al., "Nickel-Catalyzed Cross Couplings of Benzylic Ammonium Salts and Boronic Acids: Sterospecific Formation of Diarylethanes via C—N Bond Activation," Journal of the American Chemical Society, vol. 135, pp. 280-285, 2013.

Iwasa et al., "Simple Isoquinoline and Benzylisoquinoline Alkaloids as Potential Antimicrobial, Antimalarial, Cytotoxic, and Anti-HIV Agents," Bioorganic & Medicinal Chemistry, vol. 9, pp. 2871-2884, 2001.

Wang et al., "Highly asymmetric dihydroxylation of 1-aryl-1'-pyridyl alkenes," Tetrahedron Letters, vol. 41, pp. 4865-4869, 2000.

Prat et al., "Deracemization of alkyl diarylmethanes using (−)-sparteine or a chiral proton source," Tetrahedron Letters, vol. 42, pp. 4515-4518, 2001.

Brivio et al., "Reactivity of benzyl radicals: The trapping of primary, secondary and tertiary benzyl radicals with heterocyclic bases," Journal of Photochemistry & Photobiology A: Chemistry, vol. 214, pp. 112-114, 2010.

Shelanski et al., "Microtubule Assembly in the Absence of Added Nucleotides," Proc. Natl. Acad. Sci., vol. 70, No. 3, pp. 765-768, Mar. 1973.

International Search Report issued in application No. PCT/EP2015/057650 dated May 28, 2015.

French Search Report issued in application No. FR 1453142 dated Sep. 3, 2014.

\* cited by examiner

CYTOTOXIC COMPOUNDS WHICH ARE INHIBITORS OF THE POLYMERISATION OF TUBULIN

FIELD OF THE INVENTION

The present invention relates to compounds which are inhibitors of the polymerisation of tubulin, to methods for the preparation thereof, and to the uses of same.

STATE OF THE ART

Cancer is a major cause of death around the world, leading to 7.6 million deaths in 2008, or about 13% of global mortality. According to WHO estimates, mortality due to cancer will continue to increase to exceed 13 million deaths in 2030. About 30% of cancer deaths are due to five principal behavioural and dietary risk factors: (i) high body-mass index, (ii) low consumption of fruits and vegetables, (iii) lack of physical exercise, (iv) addiction to smoking and (v) alcohol consumption. Cancer can be reduced and checked by applying strategies founded on evidence-based prevention, early detection, patient care and specific treatments. Concerning the latter point, three principal methods of cancer treatment exist: surgery, radiotherapy and chemotherapy. For certain types of cancers, it is also possible to call upon hormone therapy, immunotherapy or recent targeted therapies. As the case may be, these methods may be prescribed alone, successively or in combination. Chemotherapy or polychemotherapy consists in using several compounds which are cytotoxic to cancer cells. Unlike surgery, they are systemic treatments which concern the whole body, not a particular organ, and which will however have repercussions on healthy cells such as side effects of varying severity.

One characteristic of cancer cells is to divide very rapidly to enable the tumour to develop. This characteristic is "targeted" by various agents which disrupt cell division, such as, for example, DNA intercalators (daunorubicin, doxorubicin, mitoxandrone, etc.), inhibitors of topoisomerases I and II which modify the tertiary structure of DNA (irinotecan, etoposide, etc.), and even mitotic spindle poisons.

The importance of microtubules as anti-cancer targets is underlined by the clinical use of several microtubule-targeting agents in cancer treatment, such as Vinca-type alkaloids of the Madagascar periwinkle and taxanes. Periwinkle alkaloids (vincristine, vinblastine, etc.) establish a specific bond to tubulin and inhibit its polymerisation into microtubules, thus preventing mitotic spindle formation. In turn, taxanes (paclitaxel, docetaxel) prevent tubulin depolymerization and also disrupt tubulin-microtubule equilibrium. Thus, mitotic spindle disassembly is blocked, which stops mitosis and leads to cell death. Docetaxel is recommended in the treatment of a large number of cancers. It is used alone or in combination with an anti-inflammatory (prednisone, etc.) in advanced prostate cancer (the leading cancer in men in France). In the case of breast cancers (the leading cancer in women), docetaxel is used alone or in combination with other anti-tumour agents (doxorubicin, trastuzumab, etc.). In non-small-cell lung cancer (the second-leading cancer in men and the third in women) it has shown its efficacy alone or combined with cis-platinum. Lastly, docetaxel, in combination with 5-fluorouracil, is given to treat cases of stomach, head and neck cancers. Taxol has found application in first-line treatments of breast cancer in combination with an anthracycline and of ovarian cancer in combination with cis-platinum.

Despite the therapeutic efficacy of these treatments, these various compounds have many side effects (alopecia, neutropenia, nausea, mucositis, muscle pain, etc.). For example, periwinkle alkaloids have been associated with problems of neuro-, haemato- and cardiotoxicity. Furthermore, resistance phenomena due to phenotypic changes of cancer cells are increasingly observed, such as, for example, in the case of hormone-independent prostate cancers treated with docetaxel.

Research has been undertaken to identify and develop novel molecules which disrupt the assembly of tubulin into microtubules.

In this context, combretastatin A-4 (CA-4), a member of the combretastatin family, natural stilbenes isolated by G. R. Pettit from the bark of a South-African willow tree, *Combretum caffrum*[1], has been identified. CA-4 is a stilbene in the Z-configuration substituted with two aromatic nuclei of type 3,4,5-trimethoxyphenyl (ring A) and 3-hydroxy-4-methoxyphenyl (ring B). CA-4 proved to be highly cytotoxic ($IC_{50}$=1-2 nM) to many human cancer lines as well as to lines resistant to conventional therapies using, for example, daunorubicin[2]. CA-4 is also a mitotic spindle poison since it strongly inhibits tubulin assembly into microtubules by binding to the colchicine site ($IC_{50}$=1 µM). It has also been shown that CA-4 exhibits a nanomolar anti-vascular[3] activity in vitro by inhibition of endothelial cell proliferation. A water-soluble prodrug of CA-4, fosbretabulin (CA-4P), is currently under phase III clinical development for treatment of thyroid cancer and under phase II clinical development for treatments of non-small-cell lung cancer and for treatments of cis-platinum-resistant ovarian cancer. Similarly, the hydrochloride of a structural analogue of CA-4, ombrabulin, is currently used to treat advanced soft tissue sarcomas.

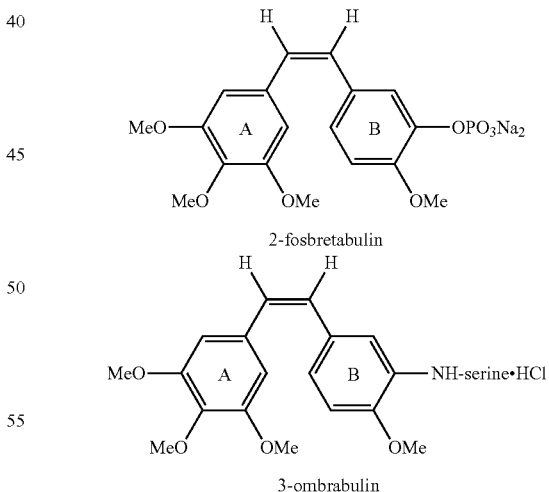

2-fosbretabulin 3-ombrabulin

While these compounds prove to be effective, they have a chemical instability attributable to isomerization of the ethylenic double bond.

Isocombretastatin A-4 (CA-4)[4], an unnatural isomer of CA-4, whose biological profile (cytotoxicity, tubulin polymerisation inhibition, induction of apoptosis, etc.) is absolutely identical to that of the natural molecule, without however exhibiting the risk of isomerization, was recently identified. This molecule, which is particularly stable, is metabolized only very little (<10%) in the presence of hepatocytes.[5]

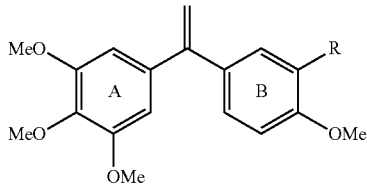

R = OH
isoCA-4

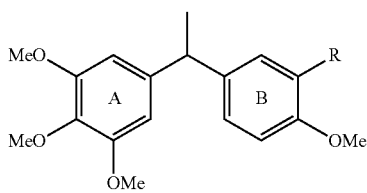

R = OH
isoerianin

It has also been shown that it is possible to reduce the double bond of isoCA-4 without a substantial loss of antitumour activity.[6] For example, isoerianin, an unnatural isomer of erianin, proved to be cytotoxic at nanomolar concentrations ($25<IG_{50}<45$ nM) on many human tumour lines and inhibits tubulin polymerisation at micromolar concentrations by blocking the cell cycle at the G2/M phase.

The combretastatin A-4 analogues synthesized to date have a 3,4,5-trimethophenyl moiety. As this group is suspected of being the cause of side effects such as neurotoxicity or cardiotoxicity, a need exists to have available novel agents which inhibit the polymerisation of tubulin. Ideally, these compounds will have to: (i) be effective at doses which exhibit little or no toxicity in man, (ii) be stable and easy to produce industrially, (iii) be water-soluble to simplify their mode of administration, (iv) have an identified mechanism of action and, (v) be free, if possible, of side effects.

BRIEF DESCRIPTION OF THE INVENTION

The present invention relates to a compound of the following formula (I):

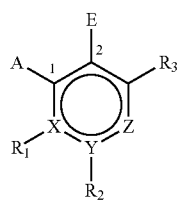

(I)

wherein:
$R_2$ and $R_3$ are different and one of the two represents a group $A_1$ of the following formula:

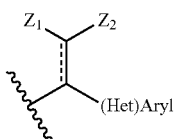

wherein:
the dashed bond is present or absent, preferably present;
$Z_1$ and $Z_2$ represent, independently of each other, a hydrogen atom, a halogen atom or a methyl group;
(Het)Aryl represents an aryl or heteroaryl group, said heteroaryl being selected from indolyl, benzothiophenyl and benzofuranyl groups, wherein said aryl or heteroaryl may be substituted with one or more substituents selected from a halogen atom, a hydroxyl group, —OMe, —SMe, —OCX$_3$ with X indicating a halogen atom, —NH$_2$,

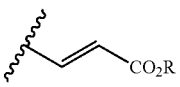

with R indicating a $C_1$-$C_6$ alkyl group,

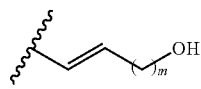

with m representing 1 or 2,

with m representing 1 or 2, and

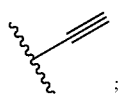

;

the other then representing:
a hydrogen atom;
a halogen atom;
a hydroxyl group;
a cyano group;
a —COYR' group with Y indicating O or N and R' indicating H or a $C_1$-$C_6$ alkyl group, a $C_2$-$C_4$ alkenyl group, a $C_2$-$C_4$ alkynyl group;
a —SO$_2$NR'R'' group with R', R'' each indicating, independently of each other, H or a $C_1$-$C_6$ alkyl group, a $C_2$-$C_4$ alkenyl group, a $C_2$-$C_4$ alkynyl group, an aryl group, a heteroaryl group;
a —NHSO$_2$R' group with R' indicating a $C_1$-$C_6$ alkyl group, a $C_2$-$C_4$ alkenyl group, a $C_2$-$C_4$ alkynyl group, an aryl group, a heteroaryl group;

a $C_1$-$C_6$ alkyl group;
a $C_2$-$C_4$ alkenyl group;
a $C_2$-$C_4$ alkynyl group;
a $C_1$-$C_6$ alkoxy group;
or a —NR'R" group with R' and R" representing, independently of each other, a hydrogen or an alkyl group;
A and E each represent a hydrogen atom or A and E take part in the structure of a fused aromatic ring of the following formula:

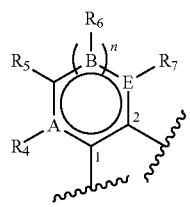

wherein A, B and E represent, independently of each other, a carbon or nitrogen atom, n represents 0 or 1 and $R_4$, $R_5$, $R_6$, $R_7$ are as described below;
X, Y and Z represent, independently of each other, a carbon or nitrogen atom provided that if X and Z represent a nitrogen atom, Y represents a carbon atom;
at least one of A, B, E, X, Y and Z represents a nitrogen atom;
$R_1$, $R_4$, $R_5$, $R_6$, $R_7$, if present, represent, independently of each other, a hydrogen atom, a halogen atom, a hydroxyl group, a $C_1$-$C_6$ alkyl group, a $C_2$-$C_4$ alkenyl group, a $C_2$-$C_4$ alkynyl group, a $C_1$-$C_6$ alkoxy group or a —NR'R" group with R' and R" representing, independently of each other, a hydrogen or a $C_1$-$C_6$ alkyl group;
as well as the pharmaceutically acceptable salts, the stereoisomers and the prodrugs thereof.

The present invention also relates to a pharmaceutical composition comprising at least one compound of the present invention.

The present invention also relates to compounds or compositions of the present invention for use as a medicine, in particular for treating or preventing proliferative diseases or as an anti-vascular medicine.

Definitions

The term "halogen", as used in the description of the present invention, refers to fluorine, chlorine, bromine and iodine atoms. Advantageously, it will be fluorine, bromine and chlorine and more advantageously fluorine or chlorine.

The term "$C_1$-$C_6$ alkyl", as used in the description of the present invention, refers to any saturated hydrocarbon group comprising 1 to 6 carbon atoms, linear or branched, particularly methyl, ethyl, n-propyl, isopropyl, n-butyl, isobutyl, sec-butyl, tert-butyl, pentyl and hexyl groups.

The term "$C_2$-$C_4$ alkenyl", as used in the description of the present invention, refers to any hydrocarbon group comprising 2 to 4 carbon atoms, linear or branched, and comprising at least one double bond, such as a vinyl (ethenyl) group.

The term "$C_2$-$C_4$ alkynyl", as used in the description of the present invention, refers to any hydrocarbon group comprising 2 to 4 carbon atoms, linear or branched, and comprising at least one triple bond, such as an ethynyl or propynyl group.

The term "$C_1$-$C_6$ alkoxy", as used in the description of the present invention, refers to any —O-alkyl group, the alkyl being as defined above. Examples of alkoxy groups include methoxy, ethoxy, propoxy, n-butoxy, iso-butoxy and tert-butoxy groups.

The term "(Het)Aryl", as used in the description of the present invention, refers to an aryl or heteroaryl.

The term "aryl", as used in the description of the present invention, refers to one or more aromatic rings having 5 to 10 carbon atoms, which may be fused. In particular, aryl groups may be monocyclic or bicyclic groups, such as for example phenyl or naphthyl groups. Advantageously, the aryl group is a phenyl.

The term "heteroaryl", as used in the description of the present invention, refers to an aromatic group comprising 5 to 10 cyclic atoms. Cyclic atoms comprise carbon atoms and one or more heteroatoms, such as for example sulphur, nitrogen or oxygen atoms. The heteroaryl according to the present invention may consist of one or two fused rings. Preferably, the heteroaryl group will be an indolyl, benzothiophenyl, benzofuranyl or benzoimidazolyl group.

The term "cyano", as used in the description of the present invention, refers to a —CN group.

The formula "—COYR", as used in the description of the present invention, refers to an acid or an ester when Y is O, an amide when Y is N.

The formula "—$SO_2$NR'R'"" or "—$NHSO_2$R'", as used in the description of the present invention, refers to a sulphonamide.

The expression "pharmaceutically acceptable", as used in the description of the present invention, refers to that which is useful in the preparation of a pharmaceutical composition, which is generally safe, nontoxic and neither biologically nor otherwise undesirable and which is acceptable for veterinary and/or human pharmaceutical use.

The expression "pharmaceutically acceptable salts", as used in the description of the present invention, refers to salts of a compound which are pharmaceutically acceptable, as defined herein, and which have the desired pharmacological activity of the parent compound. Such salts include:

(1) hydrates and solvates,
(2) acid addition salts formed with inorganic acids such as hydrochloric acid, hydrobromic acid, sulphuric acid, nitric acid, phosphoric acid and the like; or formed with organic acids such as acetic acid, benzenesulfonic acid, benzoic acid, camphosulfonic acid, citric acid, ethanesulfonic acid, fumaric acid, glucoheptonic acid, gluconic acid, glutamic acid, glycolic acid, hydroxynaphthoic acid, 2-hydroxy-ethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like. Advantageously, it is hydrochloric acid; or (3) salts formed when an acidic proton present in the parent compound either is replaced with a metal ion, for example an alkaline metal ion, an alkaline-earth metal ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide. Advantageously, the acidic proton is displaced by a $Na^+$ ion, particularly using sodium hydroxide. Acid addition salts are formed particularly with an amine functional group or a pyridine. Base addition salts are formed particularly with a carboxylic acid (—COOH), phosphate (—OP(O)(OH)$_2$) or sulphate (—OSO$_3$H) functional group.

The term "stereoisomers", as used in the description of the present invention, refers to diastereoisomers or enantiomers. They are thus configurational isomers. Stereoisomers which are not mirror images of one another are thus referred to as "diastereoisomers", and stereoisomers which are mirror images of one another but are non-superimposable are referred to as "enantiomers", also called "optical isomers". A carbon atom linked to four non-identical substituents is called a "chiral centre". When a molecule has such a chiral centre, it is called chiral and has two enantiomer forms. When a molecule has several chiral centres, then it will have several diastereoisomer and enantiomer forms. An equimolar mixture of two enantiomers is called a racemic mixture.

The term "prodrug", as used in the description of the present invention, refers to a compound which is administered in an inactive (or less active) form and which is metabolized in vivo, particularly by the action of enzymes or gastric acid, in an active (or more active) form. The use of a prodrug improves in particular the physicochemical parameters of a molecule, such as solubility, as well as the pharmacokinetics (vectorization, bioavailability, etc.), in order to promote its assimilation by an organism after administration. In particular, a prodrug of a molecule bearing an amino group (NH$_2$) can result particularly from the acylation or the phosphorylation of this amino group. When a molecule bears a hydroxy group (OH), the prodrug can result particularly from the acylation or the phosphorylation of this hydroxy group.

The expression "compounds of the present invention" as used in the present description refers to compounds of formula (I), (I'), (Ib) or (Ic) as defined in a detailed manner below.

DETAILED DESCRIPTION OF THE INVENTION

The inventors have shown that compounds of the present invention disrupt the assembly of tubulin into microtubules. These compounds have nanomolar cytotoxic activities on various human cancer lines, including lines resistant to common treatments. These compounds inhibit the polymerisation of tubulin at micromolar concentrations, even sub-micromolar concentrations, thus constituting therapeutic compounds of choice.

Due to their chemical structure, compounds of the present invention have a low risk of being metabolized, unlike CA-4 derivatives which are subject to (i) demethylation reactions on the 3,4,5-trimethoxyphenyl ring or (ii) isomerization of the double bond leading to a substantial loss of activity.

Compounds of the Present Invention

The invention thus has as an object compounds of the following formula (I):

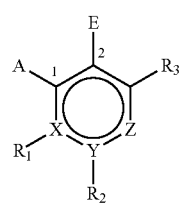

wherein:
R$_2$ and R$_3$ are different and one of the two represents a group A$_1$ of the following formula:

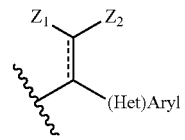

wherein:
the dashed bond is present or absent, preferably present;
Z$_1$ and Z$_2$ represent, independently of each other, a hydrogen atom, a halogen atom or a methyl group;
(Het)Aryl represents an aryl or heteroaryl group, said heteroaryl being selected from indolyl, benzothiophenyl and benzofuranyl groups, wherein said aryl or heteroaryl may be substituted with one or more substituents selected from a halogen atom, a hydroxyl group, —OMe, —SMe, —OCX$_3$ with X indicating a halogen atom, —NH$_2$,

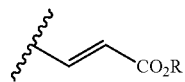

with R indicating a C$_1$-C$_6$ alkyl group,

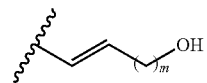

with m representing 1 or 2,

with m representing 1 or 2, and

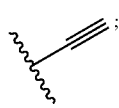 [SMILES: *C#C]

the other representing:
a hydrogen atom;
a halogen atom;
a hydroxyl group;
a cyano group;
a —COYR' group with Y indicating O or N and R' indicating H or a C$_1$-C$_6$ alkyl group, a C$_2$-C$_4$ alkenyl group, a C$_2$-C$_4$ alkynyl group;
a —SO$_2$NR'R" group with R', R" each indicating, independently of each other, H or a C$_1$-C$_6$ alkyl group, a C$_2$-C$_4$ alkenyl group, a C$_2$-C$_4$ alkynyl group;

a —NHSO$_2$R' group with R' indicating a C$_1$-C$_6$ alkyl group, a C$_2$-C$_4$ alkenyl group, a C$_2$-C$_4$ alkynyl group, an aryl group, a heteroaryl group;
a C$_1$-C$_6$ alkyl group;
a C$_2$-C$_4$ alkenyl group;
a C$_2$-C$_4$ alkynyl group;
a C$_1$-C$_6$ alkoxy group; or
a —NR'R" group with R' and R" representing, independently of each other, a hydrogen or an alkyl group;

A and E each represent a hydrogen atom or A and E take part in the structure of a fused aromatic ring of the following formula:

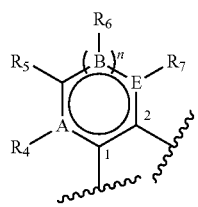

wherein A, B and E represent, independently of each other, a carbon or nitrogen atom, n represents 0 or 1 and R$_4$, R$_5$, R$_6$, R$_7$ are as described below;

X, Y and Z represent, independently of each other, a carbon or nitrogen atom provided that if X and Z represent a nitrogen atom, Y represents a carbon atom;

at least one of A, B, E, X, Y and Z represents a nitrogen atom;

R$_1$, R$_4$, R$_5$, R$_6$, R$_7$, if present, represent, independently of each other:
a hydrogen atom;
a halogen atom;
a hydroxyl group;
a C$_1$-C$_6$ alkyl group;
a C$_2$-C$_4$ alkenyl group;
a C$_2$-C$_4$ alkynyl group;
a C$_1$-C$_6$ alkoxy group; or
a —NR'R" group with R' and R" representing, independently of each other, a hydrogen or a C$_1$-C$_6$ alkyl group;

as well as the pharmaceutically acceptable salts, the stereoisomers and the prodrugs thereof.

Preferably, the invention has as an object compounds of the following formula (I'):

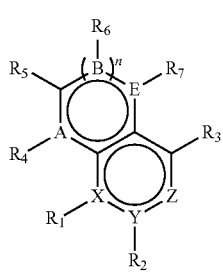

(I')

wherein:
n represents 0 or 1;
A, B and E represent, independently of each other, a carbon or nitrogen atom;
X, Y and Z represent, independently of each other, a carbon or nitrogen atom provided that if X and Z represent a nitrogen atom, Y represents a carbon atom;
at least one of A, B, E, X, Y and Z represents a nitrogen atom;

R$_1$, R$_4$, R$_5$, R$_6$, R$_7$, if present, represent, independently of each other:
a hydrogen atom;
a halogen atom;
a hydroxyl group;
a C$_1$-C$_6$ alkyl group;
a C$_2$-C$_4$ alkenyl group;
a C$_2$-C$_4$ alkynyl group;
a C$_1$-C$_6$ alkoxy group; or
a —NR'R" group with R' and R" representing, independently of each other, a hydrogen or a C$_1$-C$_6$ alkyl group;

R$_2$ and R$_3$ are different and one of the two represents a group A$_1$ of the following formula:

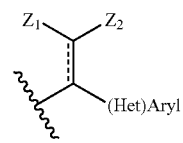

wherein:
the dashed bond is present or absent, preferably present;
Z$_1$ and Z$_2$ represent, independently of each other, a hydrogen atom, a halogen atom or a methyl group;
(Het)Aryl represents an aryl or heteroaryl group, said heteroaryl being selected from indolyl, benzothiophenyl and benzofuranyl groups, wherein said aryl or heteroaryl may be substituted with one or more substituents selected from a halogen atom, a hydroxyl group, —OMe, —SMe, —OCX$_3$ with X indicating a halogen atom, —NH$_2$,

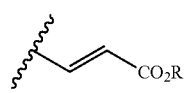

with R indicating a C$_1$-C$_6$ alkyl group,

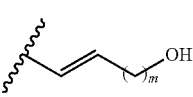

with m representing 1 or 2,

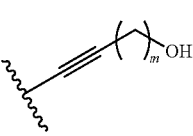

with m representing 1 or 2, and

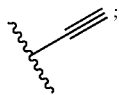

and the other represents:
- a hydrogen atom;
- a halogen atom;
- a hydroxyl group;
- a cyano group;
- a —COYR' group with Y indicating O or N and R' indicating H or a $C_1$-$C_6$ alkyl group, a $C_2$-$C_4$ alkenyl group, a $C_2$-$C_4$ alkynyl group;
- a —SO$_2$NR'R" group with R', R" each indicating, independently of each other, H or a $C_1$-$C_6$ alkyl group, a $C_2$-$C_4$ alkenyl group, a $C_2$-$C_4$ alkynyl group;
- a —NHSO$_2$R' group with R' indicating a $C_1$-$C_6$ alkyl group, a $C_2$-$C_4$ alkenyl group, a $C_2$-$C_4$ alkynyl group, an aryl group, a heteroaryl group;
- a $C_1$-$C_6$ alkyl group;
- a $C_2$-$C_4$ alkenyl group;
- a $C_2$-$C_4$ alkynyl group;
- a $C_1$-$C_6$ alkoxy group;
- a —NR'R" group with R' and R" representing, independently of each other, a hydrogen or a $C_1$-$C_6$ alkyl group;

as well as the pharmaceutically acceptable salts, the stereoisomers and the prodrugs thereof.

The expression "$R_1$, $R_4$, $R_5$, $R_6$ or $R_7$, if present", as used in the description of the present invention, means that the $R_1$, $R_4$, $R_5$, $R_6$ or $R_7$ groups will be present if the valency of the atom to which the group is, or would be bound allows it. Persons skilled in the art will be able easily to determine if such a group is present.

In certain embodiments, the invention has as an object compounds of formula (I') as represented above wherein $R_3$ is a group $A_1$ as represented above, or compounds of the following formula (Ib):

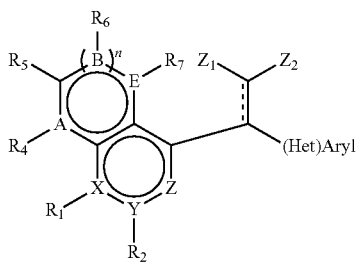

(Ib)

wherein:
n, A, B, E, X, Y, Z, $R_1$, $R_4$, $R_5$, $R_6$, $R_7$, (Het)Aryl, $Z_1$ and $Z_2$ are as described above; and $R_2$ represents:
- a hydrogen atom;
- a halogen atom;
- a hydroxyl group;
- a cyano group;
- a —COYR' group with Y indicating O or N and R' indicating H or a $C_1$-$C_6$ alkyl group, a $C_2$-$C_4$ alkenyl group, a $C_2$-$C_4$ alkynyl group;
- a SO$_2$NR'R" group with R', R" each indicating, independently of each other, H or a $C_1$-$C_6$ alkyl group, a $C_2$-$C_4$ alkenyl group, a $C_2$-$C_4$ alkynyl group;
- a —NHSO$_2$R' group with R' indicating a $C_1$-$C_6$ alkyl group, a $C_2$-$C_4$ alkenyl group, a $C_2$-$C_4$ alkynyl group, an aryl group, a heteroaryl group;
- a $C_1$-$C_6$ alkyl group;
- a $C_2$-$C_4$ alkenyl group;
- a $C_2$-$C_4$ alkynyl group;
- a $C_1$-$C_6$ alkoxy group;
- or a —NR'R" group with R' and R" representing, independently of each other, a hydrogen or an alkyl group.

In certain embodiments, the invention has as an object compounds of formula (I') or (Ib) wherein the (Het)Aryl group represents a phenyl group which may be substituted with one or more substituents selected from a halogen atom, a hydroxyl group, —OMe, —SMe, —OCX$_3$ with X indicating a halogen atom, —NH$_2$,

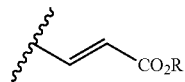

with R indicating a $C_1$-$C_6$ alkyl group,

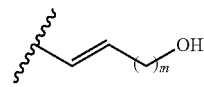

with m representing 1 or 2,

with m representing 1 or 2 and

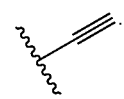 [SMILES: *C#C]

Preferably, the (Het)Aryl group represents a substituted phenyl group having the following formula:

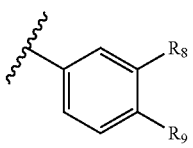

wherein:
$R_8$ represents a hydrogen atom, a halogen atom, a hydroxyl group, —OMe, —SMe, —NH$_2$,

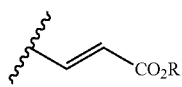

with R indicating a $C_1$-$C_6$ alkyl group,

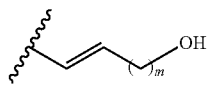

with m representing 1 or 2,

with m representing 1 or 2 or

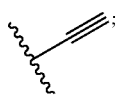;

and $R_9$ represents a $C_1$-$C_6$ alkoxy group, particularly —OMe, —SMe or —OCX$_3$ with X indicating a halogen atom.

Preferably, $R_8$ represents a hydrogen atom, a halogen atom, preferably fluorine or chlorine, a hydroxyl group or a —NH$_2$ group.

Preferably, $R_9$ represents a $C_1$-$C_6$ alkoxy group, preferably $C_1$-$C_4$, preferably methoxy, —SMe or —OCX$_3$ with X indicating a halogen atom, preferably fluorine.

Thus, in certain embodiments, the invention has as an object compounds of the following formula (Ic):

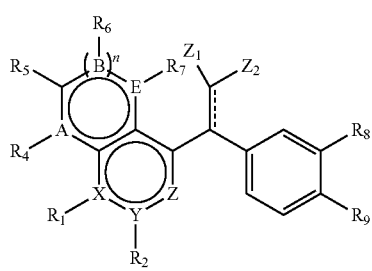

(Ic)

wherein:
n, A, B, E, X, Y, Z, $R_1$, $R_4$, $R_5$, $R_6$, $R_7$ are as described above;

$R_2$ represents:
- a hydrogen atom;
- a halogen atom;
- a hydroxyl group;
- a cyano group;
- a —COYR' group with Y indicating O or N and R' indicating H or a $C_1$-$C_6$ alkyl group, a $C_2$-$C_4$ alkenyl group, a $C_2$-$C_4$ alkynyl group;
- a —SO$_2$NR'R" group with R', R" each indicating, independently of each other, H or a $C_1$-$C_6$ alkyl group, a $C_2$-$C_4$ alkenyl group, a $C_2$-$C_4$ alkynyl group;
- a —NHSO$_2$R' group with R' indicating a $C_1$-$C_6$ alkyl group, a $C_2$-$C_4$ alkenyl group, a $C_2$-$C_4$ alkynyl group, an aryl group, a heteroaryl group;
- a $C_1$-$C_6$ alkyl group;
- a $C_2$-$C_4$ alkenyl group;
- a $C_2$-$C_4$ alkynyl group;
- a $C_1$-$C_6$ alkoxy group;
- or a —NR'R" group with R' and R" representing, independently of each other, a hydrogen or an alkyl group;

the dashed bond is absent or present, preferably present;
$Z_1$ and $Z_2$ represent, independently of each other, a hydrogen atom, a halogen atom or a methyl group;
$R_8$ represents a hydrogen atom, a halogen atom, a hydroxyl, —OMe, —SMe, —NH$_2$,

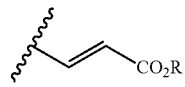

with R indicating a $C_1$-$C_6$ alkyl group,

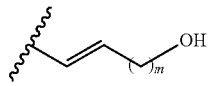

with m representing 1 or 2,

with m representing 1 or 2 or

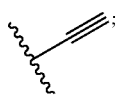;

and $R_9$ represents a $C_1$-$C_6$ alkoxy group, particularly —OMe, —SMe or —OCX$_3$ with X indicating a halogen atom;
as well as the pharmaceutically acceptable salts, the stereoisomers and the prodrugs thereof.

Preferably, in the formula (Ic) above, $R_8$ represents a hydrogen atom, a halogen atom, preferably fluorine or chlorine, a hydroxyl group, a —NH$_2$ group, or

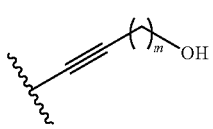

with m representing 1 or 2.

Preferably, in the formula (Ic) above, $R_9$ represents a $C_1$-$C_6$ alkoxy group, preferably $C_1$-$C_4$, preferably methoxy, —SMe or —OCX$_3$ with X indicating a halogen atom, preferably fluorine.

In the formulas (I), (I'), (Ib) and (Ic) above, groups $R_1$, $R_4$, $R_5$, $R_6$ and $R_7$ when present and group $R_2$ or $R_3$ when different from $A_1$ represent, independently of each other, preferably:
- a hydrogen atom;
- a halogen atom, preferably chlorine or fluorine;
- a hydroxyl group;
- a cyano group;
- a —COYR' group with Y indicating O or N and R' indicating H or a $C_1$-$C_6$ alkyl group, a $C_2$-$C_4$ alkenyl group, a $C_2$-$C_4$ alkynyl group;
- a —SO$_2$NR'R" group with R', R" each indicating, independently of each other, H or a $C_1$-$C_6$ alkyl group, a $C_2$-$C_4$ alkenyl group, a $C_2$-$C_4$ alkynyl group;
- a —NHSO$_2$R' group with R' indicating a $C_1$-$C_6$ alkyl group, a $C_2$-$C_4$ alkenyl group, a $C_2$-$C_4$ alkynyl group, an aryl group, a heteroaryl group;
- a $C_1$-$C_6$ alkyl group, preferably a $C_1$-$C_4$ alkyl group, preferably a methyl;
- a $C_1$-$C_6$ alkoxy group, preferably a $C_1$-$C_4$ alkoxy group, preferably the methoxy group; or
- a —NR'R" group with R' and R" representing, independently of each other, a hydrogen or a $C_1$-$C_6$ alkyl group, preferably $C_1$-$C_4$, preferably —NH$_2$ or —N(CH$_3$)$_2$.

Preferably, compounds of the present invention have the formula (I), (I'), (Ib) or (Ic) wherein $Z_1$ and $Z_2$ are identical and represent a hydrogen or fluorine atom.

Preferably, the dashed bond is present.

In certain embodiments, compounds of the present invention have the formula (I') represented above wherein:
- n, A, B, E, X, Y, Z, $R_1$, $R_4$, $R_5$, $R_6$, $R_7$, are as described above; and
- $R_2$ or $R_3$ represents a group $A_2$ of the following formula:

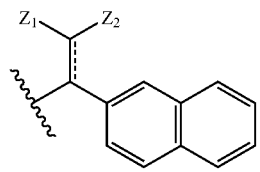

wherein:
- the dashed bond is present or absent, preferably present;
- $Z_1$ and $Z_2$ represent, independently of each other, a hydrogen atom, a halogen atom or a methyl group.

In certain embodiments, compounds of the present invention have the formula (I') represented above wherein:
- n, A, B, E, X, Y, Z, $R_1$, $R_4$, $R_5$, $R_6$, $R_7$, are as described above; and
- $R_2$ or $R_3$ represent a group $A_3$ of the following formula:

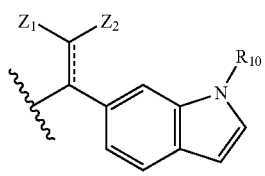

wherein:
- the dashed bond is present or absent, preferably present;
- $Z_1$ and $Z_2$ represent, independently of each other, a hydrogen atom, a halogen atom or a methyl group.
- $R_{10}$ represents a hydrogen atom or a methyl group.

In certain embodiments, compounds of the present invention have the formula (I'), (Ib) or (Ic) represented above wherein:
- n is equal to 1;
- X is a nitrogen atom;
- Z is a carbon atom or a nitrogen atom;
- A and E are, independently of each other, a nitrogen or carbon atom; and
- Y and B are a carbon atom.

In these embodiments, preferably, $R_5$ is a hydrogen atom and $R_7$, if present, is a hydrogen atom.

In particular, compounds of the present invention may have the formula (I'), (Ib) or (Ic) represented above wherein:
- n is equal to 1, X and Z are a nitrogen atom and A, E, Y and B are a carbon atom;
- n is equal to 1, X is a nitrogen atom and A, E, Z, Y and B are a carbon atom;
- n is equal to 1, Z is a nitrogen atom and A, E, X, Y and B are a carbon atom;
- n is equal to 1, X, Z and E are a nitrogen atom and A, Y and B are a carbon atom; or
- n is equal to 1, X, Z and A are a nitrogen atom and E, Y and B are a carbon atom.

In particular, compounds of the present invention may have the formula (I'), (Ib) or (Ic) represented above wherein:
- n is equal to 1, X and Z are a nitrogen atom and A, E, Y and B are a carbon atom;
- n is equal to 1, X is a nitrogen atom and A, E, Z, Y and B are a carbon atom Preferably, when n is equal to 1, X and Z are a nitrogen atom and A, E, Y and B are a carbon atom, compounds of the present invention have the formula (I'), (Ib) or (Ic) represented above wherein $R_4$, $R_5$, $R_6$ and $R_7$ represent a hydrogen atom. In certain embodiments, compounds of the present invention have the formula (Ib) or (Ic) wherein n is equal to 1, X and Z are a nitrogen atom, A, E, Y and B are a carbon atom, $R_4$, $R_5$, $R_6$ and $R_7$ represent a hydrogen atom and $R_2$ is as defined above. Preferably, $R_2$ is different from a hydrogen atom. In other embodiments, compounds of the present invention have the formula (I') wherein n is equal to 1, X and Z are a nitrogen atom, A, E, Y and B are a carbon atom, $R_4$, $R_5$, $R_6$ and $R_7$ represent a hydrogen atom, $R_2$ is a group $A_1$ as defined above and $R_3$ is as defined above, preferably $R_3$ is different from a hydrogen atom.

Preferably, when n is equal to 1, X is a nitrogen atom and A, E, Z, Y and B are a carbon atom, compounds of the present invention have the formula (I'), (Ib) or (Ic) represented above wherein $R_4$, $R_5$, $R_6$ and $R_7$ represent a hydrogen atom. In certain embodiments, compounds of the present invention have the formula (Ib) or (Ic) wherein n is equal to 1, X is a nitrogen atom, A, E, Z, Y and B are a carbon atom, $R_4$, $R_5$, $R_6$ and $R_7$ represent a hydrogen atom and $R_2$ is as defined above. Preferably, $R_2$ is different from a hydrogen atom. In other embodiments, compounds of the present invention have the formula (I') wherein n is equal to 1, X is a nitrogen atom, A, E, Z, Y and B are a carbon atom, $R_4$, $R_5$, $R_6$ and $R_7$ represent a hydrogen atom, $R_2$ is a group $A_1$ as defined above and $R_3$ is as defined above, preferably $R_3$ is different from a hydrogen atom.

Preferably, when n is equal to 1, X, Z and E are a nitrogen atom and A, Y and B are a carbon atom, compounds of the present invention have the formula (I'), (Ib) or (Ic) represented above wherein $R_4$, $R_5$ and $R_6$ represent a hydrogen atom. In certain embodiments, compounds of the present invention have the formula (Ib) or (Ic) wherein n is equal to 1, X, Z and E are a nitrogen atom, A, Y and B are a carbon atom, $R_4$, $R_5$ and $R_6$ represent a hydrogen atom and $R_2$ is as defined above. Preferably, $R_2$ is different from a hydrogen atom. In other embodiments, compounds of the present invention have the formula (I) wherein n is equal to 1, X, Z and E are a nitrogen atom, A, Y and B are a carbon atom, $R_4$, $R_5$ and $R_6$ represent a hydrogen atom, $R_2$ is a group $A_1$ as defined above and $R_3$ is as defined above, preferably $R_3$ is different from a hydrogen atom.

Preferably, when n is equal to 1, X, Z and A are a nitrogen atom and E, Y and B are a carbon atom, compounds of the present invention have the formula (I'), (Ib) or (Ic) represented above wherein $R_5$, $R_6$ and $R_7$ are a hydrogen atom.

In certain embodiments, compounds of the present invention have the formula (Ib) or (Ic) wherein n is equal to 1, X, Z and A are a nitrogen atom and E, Y and B are a carbon atom, $R_5$, $R_6$ and $R_7$ are a hydrogen atom and $R_2$ is as defined above. Preferably, $R_2$ is different from a hydrogen atom. In other embodiments, compounds of the present invention have the formula (I') wherein n is equal to 1, X, Z and A are a nitrogen atom and E, Y and B are a carbon atom, $R_5$, $R_6$ and $R_7$ is a hydrogen atom, $R_2$ is a group $A_1$ as defined above and $R_3$ is as defined above, preferably $R_3$ is different from a hydrogen atom.

In certain embodiments, compounds of the present invention have the formula (I'), (Ib) or (Ic) represented above wherein:
n is equal to 0;
A and X are nitrogen atoms;
E and Z are, independently of each other, a nitrogen or carbon atom; and
Y is a carbon atom.

In these embodiments, preferably, $R_5$ is a hydrogen atom and $R_7$, if present, is a hydrogen atom.

In particular, compounds of the present invention may have the formula (I'), (Ib) or (Ic) represented above wherein:
n is equal to 0, A, X, E and Z are a nitrogen atom and Y is a carbon atom;
n is equal to 0, A, X and Z are a nitrogen atom and E and Y are a carbon atom; or
n is equal to 0, A and X are a nitrogen atom and E, Y and Z are a carbon atom.

Preferably, when n is equal to 0, A, X, E and Z are a nitrogen atom and Y is a carbon atom, compounds of the present invention have the formula (I'), (Ib) or (Ic) represented above wherein $R_5$ is a hydrogen atom and $R_4$ and $R_2$ are as defined above, preferably $R_4$ and $R_2$ are different from a hydrogen atom.

Preferably, when n is equal to 0, A, X and Z are a nitrogen atom and E and Y are a carbon atom, compounds of the present invention have the formula (I'), (Ib) or (Ic) represented above wherein $R_2$, $R_5$ and $R_7$ are a hydrogen atom and $R_4$ is as defined above, preferably $R_4$ is different from a hydrogen atom.

Preferably, when n is equal to 0, A and X are a nitrogen atom and E, Y and Z are a carbon atom, compounds of the present invention have the formula (I'), (Ib) or (Ic) represented above wherein $R_2$, $R_5$ and $R_7$ are a hydrogen atom and $R_4$ is as defined above, preferably $R_4$ is different from a hydrogen atom.

In certain embodiments, compounds of the present invention have the formula (I'), (Ib) or (Ic) represented above wherein:
n is equal to 1;
A, B, E, Y and Z are a carbon atom;
X is a nitrogen atom.

In these embodiments, preferably, $R_4$, $R_5$, $R_6$ and $R_7$ represent a hydrogen atom.

In particular, compounds of the present invention may have the formula (Ib) or (Ic) represented above wherein n is equal to 1, A, B, E, Y and Z are a carbon atom, X is a nitrogen atom and $R_2$ is as defined above, preferably $R_2$ is different from a hydrogen atom.

In certain embodiments, compounds of the present invention have the formula (I'), (Ib) or (Ic) represented above wherein:
n is equal to 1;
A, B, E, Y and X are a carbon atom;
Z is a nitrogen atom.

In these embodiments, preferably, $R_4$, $R_5$, $R_6$ and $R_7$ represent a hydrogen atom.

In particular, compounds of the present invention may have the formula (Ib) or (Ic) represented above wherein n is equal to 1, A, B, E, Y and X are a carbon atom, Z is a nitrogen atom and $R_2$ is as defined above, preferably $R_2$ is different from a hydrogen atom.

In certain embodiments, compounds of the present invention have the formula (I'), (Ib) or (Ic) represented above wherein:
n is equal to 1;
A, B, E and X are a carbon atom;
Y and Z are a nitrogen atom.

In these embodiments, preferably, $R_4$, $R_5$, $R_6$ and $R_7$ represent a hydrogen atom.

In particular, compounds of the present invention may have the formula (Ib) or (Ic) represented above wherein n is equal to 1, A, B, E and X are a carbon atom, Y and Z are a nitrogen atom and $R_1$ is as defined above, preferably $R_1$ is different from a hydrogen atom.

In certain embodiments, compounds of the present invention have the formula (I'), (Ib) or (Ic) represented above wherein:
n is equal to 1;
X, Y, Z and E are a carbon atom;
A and B are a nitrogen atom.

In these embodiments, preferably, $R_1$, $R_2$ and $R_7$ represent a hydrogen atom.

In particular, compounds of the present invention may have the formula (Ib) or (Ic) represented above wherein n is equal to 1, X, Y, Z and E are a carbon atom, A and B are a nitrogen atom and $R_5$ is as defined above, preferably $R_5$ is different from a hydrogen atom.

In certain embodiments, compounds of the present invention have the formula (I'), (Ib) or (Ic) represented above wherein:
n is equal to 1;
A, B and E represent a carbon atom; and
X, Y, Z, $R_1$, $R_2$, $R_3$, $R_4$, $R_5$, $R_6$ and $R_7$ are as described above.

In certain embodiments, compounds of the present invention have the formula (I'), (Ib) or (Ic) represented above wherein:
n is equal to 1;
A, B and E represent a carbon atom;
$R_4$, $R_5$, $R_6$ and $R_7$ represent a hydrogen; and
X, Y, Z, $R_1$, $R_2$ and $R_3$ are as described above.

In certain embodiments, compounds of the present invention have the formula (I'), (Ib) or (Ic) represented above wherein:

n is equal to 1;
A, B and E represent a carbon atom;
$R_4$, $R_5$, $R_6$ and $R_7$ represent a hydrogen;
X and Y represent a nitrogen atom;
Z represents a carbon atom; and
$R_1$, $R_2$ and $R_3$ are as described above.

In certain embodiments, compounds of the present invention have the formula (I'), (Ib) or (Ic) represented above wherein:
n is equal to 1;
A, B and E represent a carbon atom;
$R_4$, $R_5$, $R_6$ and $R_7$ represent a hydrogen;
X and Y represent a nitrogen atom;
Z represents a carbon atom;
$R_1$ is absent;
$R_2$ represents a hydrogen, a halogen, a $C_1$-$C_6$ alkyl group, a $C_2$-$C_4$ alkenyl group, a $C_2$-$C_4$ alkynyl group, a $C_1$-$C_6$ alkoxy group or a —NR'R" group with R' and R" representing, independently of each other, a hydrogen or an alkyl group; and
$R_3$ is as described above.

In certain particular embodiments, compounds of the present invention have one of the following formulas:

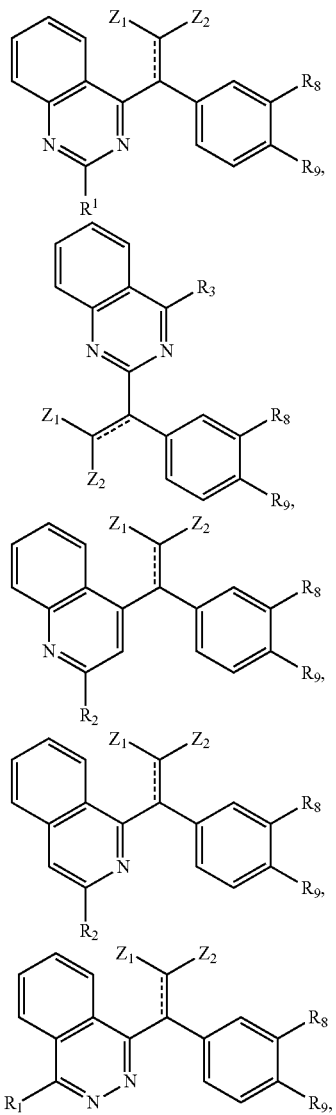

-continued

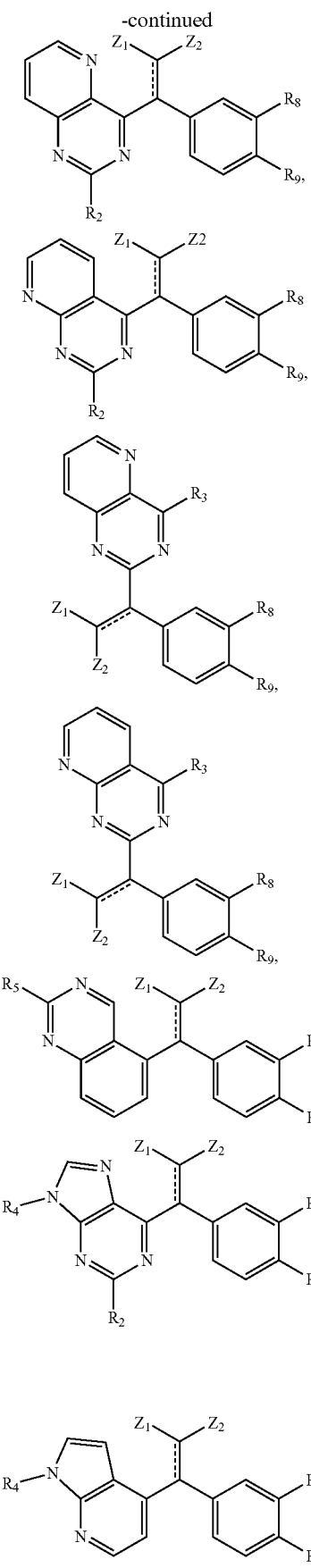

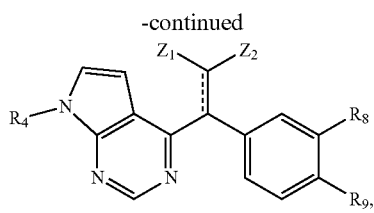

wherein, in an appropriate manner, $Z_1$, $Z_2$, $R_1$, $R_2$, $R_3$, $R_4$, $R_5$, $R_8$ and $R_9$ are as defined above and the dashed bond is absent or present. Preferably, the dashed bond is present.

In particular, in certain embodiments, $Z_1$ and $Z_2$ each represent a hydrogen or each a fluorine atom and $R_1$, $R_2$, $R_3$, $R_4$, $R_5$, $R_8$ and $R_9$ are as defined above.

In other embodiments, $R_9$ indicates a methoxy and $Z_1$, $Z_2$, $R_1$, $R_2$, $R_3$, $R_4$, $R_5$ and $R_8$ are as defined above.

In other embodiments, $Z_1$ and $Z_2$ each represent a hydrogen or each a fluorine atom, $R_9$ represents a methoxy and $R_1$, $R_2$, $R_3$, $R_4$, $R_5$ and $R_8$ are as defined above.

In particular, compounds of the invention may be selected from:

I-1
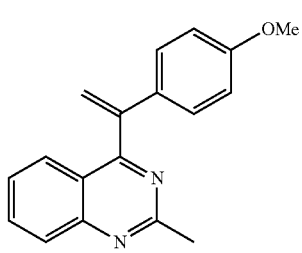 [SMILES: C=C(c1ccc(OC)cc1)c1nc(C)nc2ccccc12]

I-2
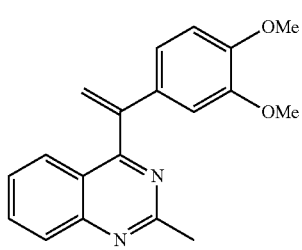 [SMILES: C=C(c1ccc(OC)c(OC)c1)c1nc(C)nc2ccccc12]

I-3
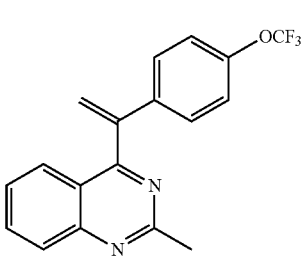 [SMILES: C=C(c1ccc(OC(F)(F)F)cc1)c1nc(C)nc2ccccc12]

I-4
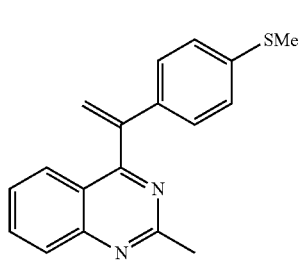 [SMILES: C=C(c1ccc(SC)cc1)c1nc(C)nc2ccccc12]

I-5
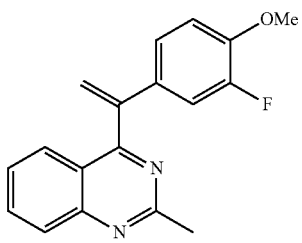 [SMILES: C=C(c1ccc(OC)c(F)c1)c1nc(C)nc2ccccc12]

I-6
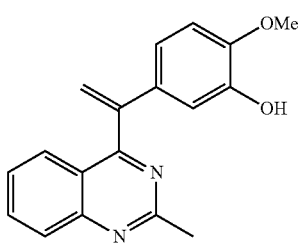 [SMILES: C=C(c1ccc(OC)c(O)c1)c1nc(C)nc2ccccc12]

I-7
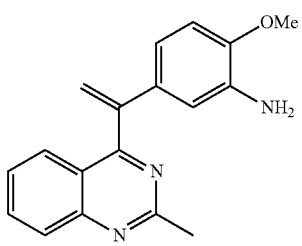

I-8
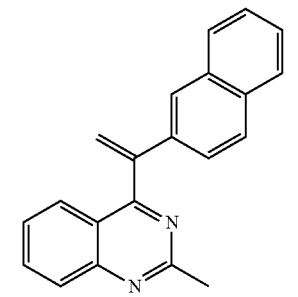 [SMILES: C=C(c1ccc2ccccc2c1)c1nc(C)nc2ccccc12]

I-9
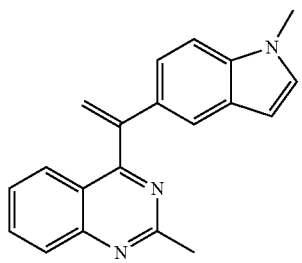

I-10
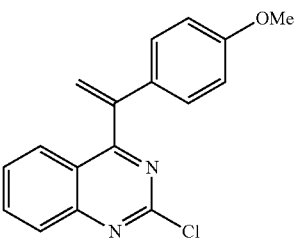 [SMILES: C=C(c1ccc(OC)cc1)c1nc(Cl)nc2ccccc12]

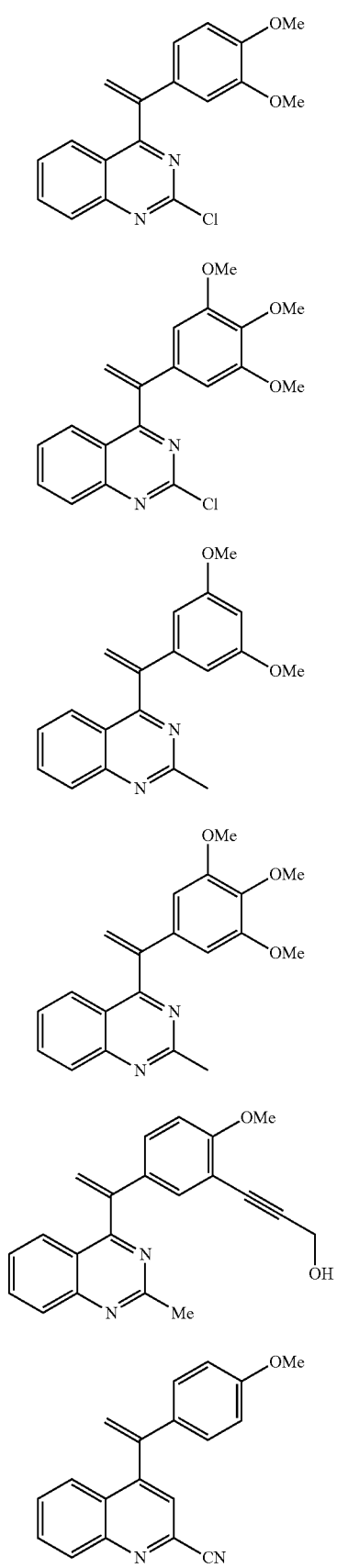
I-11
I-12
I-13
I-14
I-15
I-16
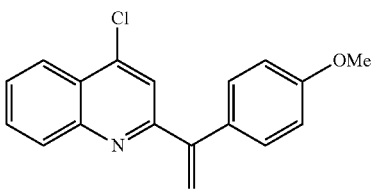 [SMILES: C=C(c1ccc(OC)cc1)c1cc(Cl)c2ccccc2n1]
I-17
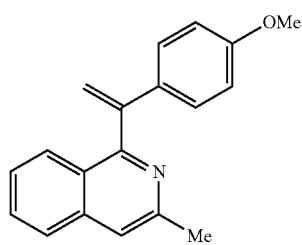 [SMILES: C=C(c1ccc(OC)cc1)c1nc(C)cc2ccccc12]
I-18
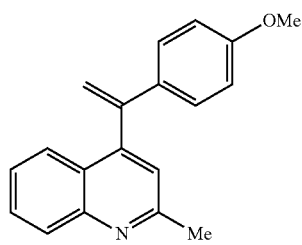 [SMILES: C=C(c1ccc(OC)cc1)c1cc(C)nc2ccccc12]
I-19
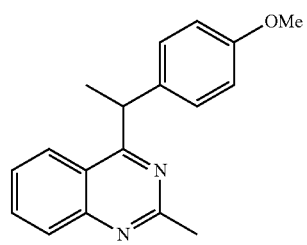
II-1
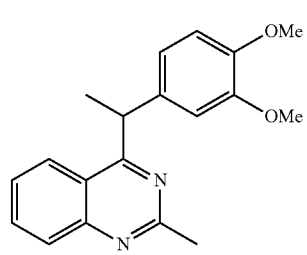
II-2
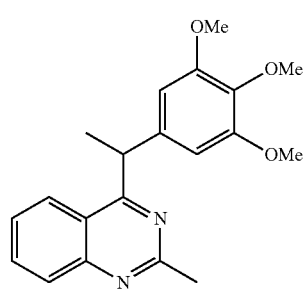
II-3

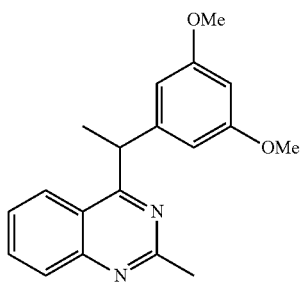

II-4

The absence of a double ethylene bond in compounds of formula (I) solves the isomerization problem likely to occur in vivo, leading to drops in (or absences of) cytotoxic activity as is the case, for example, of CA-4. Reduction of the double bond located between the two aromatic nuclei yields derivatives which are less cytotoxic than their precursors.

Method for Synthesizing Compounds of the Present Invention

The invention also has as an object the methods for synthesizing compounds of the present invention. The synthesis methods are short, advantageously comprising 2 to 3 steps. These methods are compatible with industrial requirements.

Coupling an easily accessible tosylhydrazone with a halogenated derivative bearing the nitrogenous bicycle gives compounds according to the invention with excellent yields, advantageously without having to resort to protection-deprotection steps.

Compounds according to the invention may be prepared according to methods known to persons skilled in the art, starting with commercially-available products or prepared according to methods known to persons skilled in the art.

In particular, compounds of formula (I), (I'), (Ib) and (Ic) may be prepared by a method comprising the following successive steps:

a) reaction of a compound of formula (II)

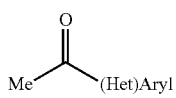
(II)

with tosylhydrazine to yield the tosylhydrazone compound of formula (III)

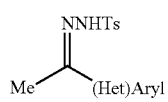
(III)

b) coupling of the compound of formula (III) with the compound of formula (IV), (V), (VI) or (VII)

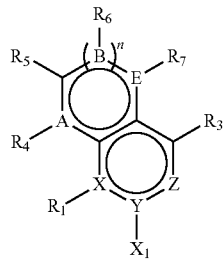
(IV)

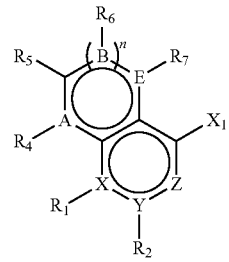
(V)

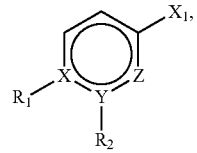
(VI)

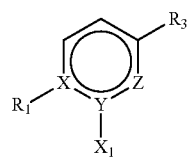
(VII)

wherein $R_1$, $R_2$, $R_3$, $R_4$, $R_5$, $R_6$, $R_7$, X, Y, Z, A, B, E and n are as previously defined and $X_1$ represents a halogen atom or trifluoromethanesulfonate;

b) if need be, reduction of compound (I), wherein the dashed double bond is present, obtained following step b) to yield compound (I) wherein the dashed double bond is absent;

c) separation from the reaction medium of compound (I) obtained following step b) or c).

Persons skilled in the art will protect, in a suitable manner, if need be, groups $R_1$ to $R_7$ so that only group $X_1$ reacts or adapt as a consequence the synthesis strategy.

For example, when groups $R_1$, $R_2$, $R_3$, $R_4$, $R_5$, $R_6$ and/or $R_7$ (if present) represent a halogen atom:

$X_1$ is an iodine atom if groups $R_1$, $R_2$, $R_3$, $R_4$, $R_5$, $R_6$ and $R_7$ (if present) are a bromine, chlorine or fluorine atom;

if groups $R_1$, $R_2$, $R_3$, $R_4$, $R_5$, $R_6$ and $R_7$ (if present) are a chlorine or fluorine atom, then $X_1$ is a bromine atom.

In particular, compounds of formula (I'), (Ib) or (Ic) wherein n is equal to 1, A, B, E and Y are carbon atoms and X and Z are nitrogen atoms may be prepared by a method comprising the following successive steps:

a) reaction of a compound of formula (II)

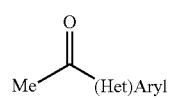
(II)

with tosylhydrazine to yield the tosylhydrazone compound of formula (III)

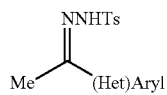
(III)

b) coupling of the compound of formula (III) with the compound of formula (IV') or (V')

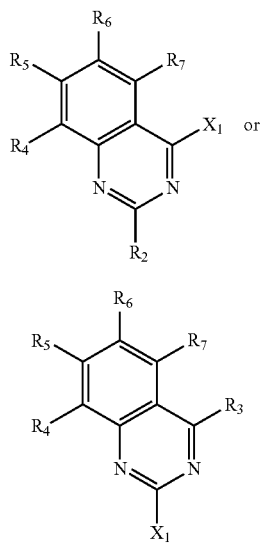

wherein $R_2$, $R_3$, $R_4$, $R_5$, $R_6$ and $R_7$ are as previously defined and $X_1$ represents a halogen atom or trifluoromethanesulfonate;

c) if need be, reduction of compound (I), wherein the dashed double bond is present, obtained following step b) to yield compound (I) wherein the dashed double bond is absent;

d) separation from the reaction medium of compound (I) obtained following step b) or c).

This step c) may be followed by possible additional conventional steps for modifying the substituents of the (Het)Aryl group and possibly of $Z_1/Z_2$.

The compound thus obtained may be separated from the reaction medium by methods well-known to persons skilled in the art, such as for example by extraction, solvent evaporation or by precipitation and filtration.

The compound may be further purified if need be by techniques well-known to persons skilled in the art, such as by recrystallization if the compound is crystalline, by distillation, by column chromatography on silica gel or by high-performance liquid chromatography (HPLC).

During step b), the coupling is advantageously carried out in the presence of a palladium complex, a ligand, in a catalytic quantity, and a base. In particular, the coupling may be carried out by means of a palladium complex such as $PdCl_2(MeCN)_2$, the ligand dppf in catalytic quantity and the base tBuOLi. In particular, the coupling may be carried out in the presence of 10% molar $PdCl_2(MeCN)_2$, 20% molar dppf, 2.2 molar equivalent tBuOLi in the presence of dioxane, at 90° C., for 2 to 4 hours.

During step c), the reduction is achieved advantageously by hydrogenation. The hydrogenation is advantageously carried out under hydrogen atmosphere, particularly in the presence of palladium on carbon (Pd/C) as catalyst or possibly $PtO_2$. Advantageously, 5 to 30 mol %, preferably about 10 mol % catalyst is used during this reaction. Moreover, ethyl acetate will advantageously be used as solvent during this step.

In particular, compounds of formula (I), (I'), (Ib) and (Ic) may be prepared by a method comprising the following successive steps:

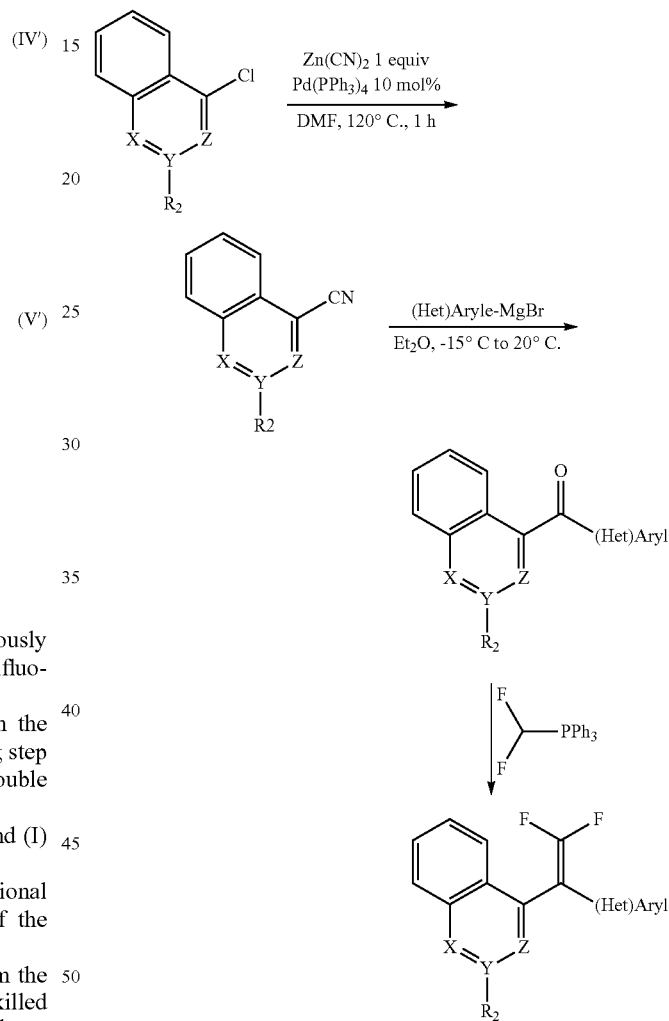

In particular, certain compounds of the present invention may be prepared according to the following scheme:

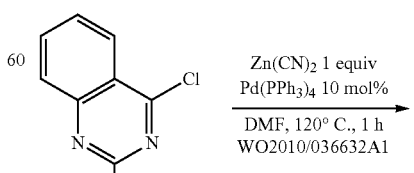

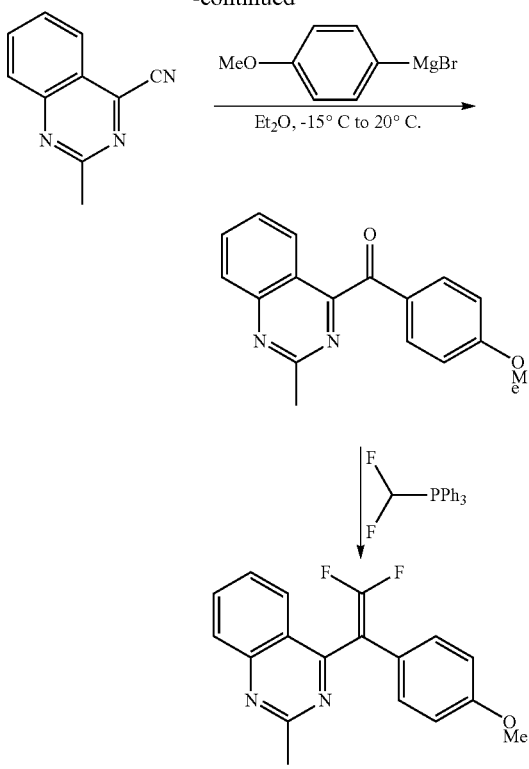

Uses of Compounds of the Present Invention

In certain aspects, the invention relates to compounds of formula (I), (Ib) or (Ic), as well as to the pharmaceutically acceptable salts, the stereoisomers and the prodrugs thereof, for use as a medicine.

In particular, compounds of the present invention may be used as medicines which inhibit the polymerisation of tubulin, advantageously as medicines for treating or preventing proliferative diseases, such as cancer, psoriasis or fibrosis, particularly cancer. In particular, compounds of the invention may be useful in the treatment of a cancer, such as those able to be treated with CA-4 or with taxotere.

Compounds of the present invention may also be used as anti-vascular medicines.

The invention also relates to a pharmaceutical composition comprising at least one compound according to the present invention, typically in combination with one or more pharmaceutically acceptable excipients.

In certain aspects, the invention also relates to a pharmaceutical composition comprising at least one compound according to the present invention in combination with at least one other active ingredient, particularly an anti-cancer compound, cytotoxic or not, and one or more pharmaceutically acceptable excipients.

In a non-limiting manner, the active ingredients able to be combined with the compound of the present invention may be selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide, lanreotide, (Z)-3-[2,4-dimethyl-5-(2-oxo-1,2-dihydro-indol-3-ylidenemethyl)-1H-pyrrol-3-yl]-propionic acid, 4-((9-chloro-7-(2,6-difluorophenyl)-5H-pyrimidol(5,4-d)(2)benzazepin-2-yl)amino)benzoic acid, 5,6-dimethylxanthenone-4-acetic acid and 3-(4-(1,2-diphenylbut-1-enyl)phenyl)acrylic acid.

The invention also concerns a pharmaceutical composition comprising at least one compound according to the present invention in combination with an antibody. The composition may comprise one or more pharmaceutically acceptable excipients. The antibody is used to target the tumour. In particular, the pharmaceutical composition may comprise at least one compound according to the present invention in combination with a monoclonal antibody. The combination of the compound of the present invention with the antibody may be achieved in the form of "antibody-compound of the present invention" conjugates. The antibody and the compound of the present invention are typically bound covalently by means of a bond. Persons skilled in the art will be able to determine the nature of the bond suited to bonding the compound of the present invention to an antibody. Thus, in one aspect, the present invention relates to a conjugate comprising a compound according to the present invention bound covalently to an antibody.

Compounds and compositions according to the invention may be administered orally, sublingually, parenterally, subcutaneously, intramuscularly, intravenously, transdermally, locally or rectally.

Compounds according to the present invention may be used at doses between 0.01 mg and 1000 mg per day, given in a single dose once per day or preferably administered in several doses throughout the day, for example twice per day in equal doses. The dose administered per day is advantageously between 5 mg and 500 mg, even more advantageously between 10 mg and 200 mg. It may be necessary to use doses outside these ranges, which persons skilled in the art will be able to determine.

Compounds according to the invention may be used to decrease or inhibit the polymerisation of tubulin, particularly in vitro and also in vivo.

The present invention also relates to a pharmaceutical composition comprising:
(i) at least one compound of the present invention,
(ii) at least one other active ingredient,
as combination products for simultaneous, separate or sequential use.

The one or more active ingredients may be such as cited above. In particular, the active ingredient may be useful for treating proliferative diseases such as cancer, psoriasis or fibrosis, advantageously an anti-cancer agent such as an anti-vascular, cytotoxic or anti-angiogenic agent.

The pharmaceutical compositions as described above may be useful for treating proliferative diseases, such as cancer, psoriasis or fibrosis, particularly cancer.

Finally, the present invention concerns a method for treating proliferative diseases, such as cancer, psoriasis or fibrosis, and particularly cancer, comprising the administration, to a patient in need thereof, of a compound of the present invention alone or in combination, advantageously synergistic, with at least one other active ingredient as defined above.

The present invention also concerns pharmaceutical compositions in the form of nanoparticle formulations. In such embodiments, the pharmaceutical compositions comprise at least one compound of the present invention coupled covalently to at least one molecule of a hydrocarbon compound having a squalene structure. In particular, the pharmaceutical compositions comprise at least one compound of the present invention coupled covalently to at least one molecule of a hydrocarbon compound having a squalene structure and a polar solvent or water.

The hydrocarbon compound having a squalene structure and the covalent coupling of this compound with compounds of the present invention may be as described in WO 2006/090029 or FR 2 924 024.

In particular, the hydrocarbon compounds having a squalene structure designate linear hydrocarbon structures made up of isoprene units, more particularly of six isoprene units. For example, the hydrocarbon compounds having a squalene structure may be squalenic acid and derivatives thereof, particularly substituted derivatives thereof. The hydrocarbon compounds having a squalene structure may bear a functional group capable of reacting with a functional group present on compounds of the present invention so as to form a covalent bond between the two compounds, particularly an ester, ether, thiether, disulphide, phosphate or amide type covalent bond. Alternatively, the covalent bond between the two compounds may be achieved by means of a linker arm. Such linker arms are well-known to persons skilled in the art.

The invention will now be illustrated, in a non-limiting manner, by the following examples.

Examples

General Procedure for Synthesizing Compounds I-1 to I-19

4-Chloroquinazoline (1 mmol) is added to a solution of N-tosylhydrazone (1.5 mmol), t-BuOLi (2.2 mmol), $PdCl_2(CH_3CN)_2$ (0.1 mmol), and dppf (0.2 mmol) in dioxane (1 mL). The reaction medium is sealed then heated at 90° C. for 2 hours before being returned to room temperature. The suspension obtained is filtered on a Celite column (eluent AcOEt) to separate the inorganic salts. After evaporation of the solvents under vacuum, the residue formed is chromatographed on a silica gel column.

4-[1-(4-Methoxy-phenyl)-vinyl]-2-methyl-quinazoline I-1

Yellow oil, 50%. TLC: Rf 0.3 (Cyclohexane/EtOAc, 7/3). IR (neat, $cm^{-1}$): 1608, 1554, 1511, 1250, 1180. $^1$H NMR (300 MHz, $CDCl_3$): 7.97 (d, 1H, J=8.5 Hz), 7.87 (d, 1H, J=8.5 Hz), 7.81 (td, 1H, J=8.5 Hz, J=0.9 Hz), 7.41 (td, 1H, J=8.3 Hz, J=0.9 Hz), 7.23 (d, 2H, J=8.9 Hz), 6.82 (d, 2H, J=8.9 Hz), 6.04 (s, 1H), 5.46 (s, 1H), 3.78 (s, 3H), 2.93 (s, 3H). $^{13}$C NMR (75 MHz, $CDCl_3$): 169.9, 164.1, 159.8, 151.1, 145.0, 133.9, 131.4, 128.1, 128.0 (2), 127.1, 126.7, 121.7, 116.9, 114.1 (2C), 55.4, 26.8. m/z MS ($ESI^+$): 277 $(M+H)^+$.

4-[1-(3,4-Dimethoxy-phenyl)-vinyl]-2-methyl-quinazoline I-2

Yellow oil, 48%. TLC: Rf 0.1 (Cyclohexane/EtOAc, 7/3). IR (neat, $cm^{-1}$): 1554, 1514, 1464, 1326, 1221, 1143. $^1$H NMR (300 MHz, $CDCl_3$): 7.96 (d, 1H, J=8.4 Hz), 7.87-7.78 (m, 2H), 7.41 (t, 1H, J=7.6 Hz), 6.97 (d, 1H, J=1.6 Hz), 6.76-6.68 (m, 2H), 6.03 (s, 1H), 5.48 (s, 1H), 3.84 (s, 3H), 3.41 (s, 3H), 2.93 (s, 3H). $^{13}$C NMR (75 MHz, $CDCl_3$): 169.7, 164.1, 151.1, 149.5, 149.1, 145.3, 133.9, 131.8, 128.1, 127.0, 126.7, 121.7, 120.1, 117.4, 111.1, 109.5, 56.0 (2C), 26.8. m/z MS ($APCI^+$): 307 $(M+H)^+$.

2-Methyl-4-(1-(4-(trifluoromethoxy)phenyl)vinyl) quinazoline I-3

Yellow oil, 78%. TLC: Rf 0.3 (Cyclohexane/EtOAc, 7/3). IR (neat, $cm^{-1}$): 1554, 1509, 1490, 1254, 1207, 1164. $^1$H NMR (300 MHz, $CDCl_3$): 8.00 (d, 1H, J=8.2 Hz), 7.85-7.82 (m, 2H), 7.49-7.43 (td, 1H, J=7.4 Hz, J=1.1 Hz), 7.36 (d, 2H, J=8.9 Hz), 7.15 (d, 2H, J=8.1 Hz), 6.16 (s, 1H), 5.62 (s, 1H), 2.93 (s, 3H). $^{13}$C NMR (75 MHz, $CDCl_3$): 169.2, 164.1, 151.1, 149.3, 144.3, 137.4, 134.3, 128.3 (2C), 128.2, 127.1, 126.7, 121.6, 121.1 (2C), 120.4 (q, J=256.5 Hz), 119.9, 26.8. $^{19}$F NMR (188 MHz, $CDCl_3$): −58.23. m/z MS ($APCI^+$): 331 $(M+H)^+$.

2-Methyl-4-(1-(4-(methylthio)phenyl)vinyl)quinazoline I-4

Yellow oil, 43%. TLC: Rf 0.4 (Cyclohexane/EtOAc, 7/3). IR (neat, $cm^{-1}$): 1751, 1554, 1492, 1326, 1215. $^1$H NMR (300 MHz, $CDCl_3$): 7.96 (d, 1H, J=8.4 Hz), 7.83-7.76 (m, 2H), 7.42-7.36 (m, 1H), 7.20 (d, 2H, J=8.6 Hz), 7.14 (d, 2H, J=8.7 Hz), 6.09 (s, 1H), 5.52 (s, 1H), 2.91 (s, 3H), 2.42 (s, 3H). $^{13}$C NMR (75 MHz, $CDCl_3$): 169.4, 164.1, 151.1, 145.0, 139.2, 135.4, 133.9, 128.1, 127.0 (2C), 126.9, 126.8, 126.3 (2C), 121.6, 118.1, 26.7, 15.5. m/z MS ($APCI^+$): 293 $(M+H)^+$.

4-[1-(3-Fluoro-4-methoxy-phenyl)-vinyl]-2-methyl-quinazoline I-5

Yellow oil, 46%. TLC: Rf 0.2 (Cyclohexane/EtOAc, 7/3). IR (neat, $cm^{-1}$): 1615, 1554, 1517, 1275, 1134, 1027. $^1$H NMR (300 MHz, $CDCl_3$): 7.99 (d, 1H, J=8.3 Hz), 7.86-7.80 (m, 2H), 7.46-7.41 (td, 1H, J=7.2 Hz, J=1.0 Hz), 7.13 (dd, 1H, J=12.5 Hz, J=2.2 Hz), 6.96-6.92 (m, 1H), 6.85 (t, 1H, J=8.5 Hz), 6.06 (s, 1H), 5.51 (s, 1H), 3.86 (s, 3H), 2.93 (s, 3H). $^{13}$C NMR (75 MHz, $CDCl_3$): 169.3, 164.1, 154.1, 150.9 (d, 1C, J=23.7 Hz), 147.9 (d, 1C, J=11.1 Hz), 144.1, 134.1, 131.9 (d, 1C, J=6.3 Hz), 128.2, 126.9, 126.8, 122.9 (d, 1CH, J=3.3 Hz), 121.6, 118.1, 114.3 (d, 1C, J=19.4 Hz), 113.3 (d, 1C, J=1.9 Hz), 56.4, 26.7. $^{19}$F NMR (188 MHz, $CDCl_3$): −132.7. m/z MS ($APCI^+$): 295 $(M+H)^+$.

2-Methoxy-5-(1-(2-methylquinazolin-4-yl)vinyl) phenol I-6

4-Chloroquinazoline (1 mmol) is added to a mixture containing silylated N-tosylhydrazone (1.5 mmol), t-BuOLi (2.2 mmol), $PdCl_2(CH_3CN)_2$ (0.1 mmol) and dppf (0.2 mmol) in dioxane (1 mL). The reaction medium is sealed then heated at 90° C. for 2 hours before being returned to room temperature. The suspension obtained is filtered on a Celite column (eluent AcOEt) to separate the inorganic salts. After evaporation of the solvents under vacuum, the residue formed is dissolved in MeOH (1 mL) then $K_2CO_3$ (2 mmol) is added and the reaction medium is stirred at room temperature for 6 hours. The suspension thus formed is filtered, the organic solvents are evaporated and the residue formed is chromatographed on a silica gel column.

Yellow oil, 34%. TLC: Rf 0.1 (Cyclohexane/EtOAc, 7/3). IR (neat, $cm^{-1}$): 1615, 1554, 1512, 1439, 1279, 1135. $^1$H NMR (300 MHz, $CDCl_3$): 7.98 (d, 1H, J=8.4 Hz), 7.87 (d, 1H, J=8.3 Hz), 7.81 (td, 1H, J=7.1 Hz, J=1.2 Hz), 7.42 (t, 1H, J=7.4 Hz), 6.92 (d, 1H), 6.75 (s, 2H), 6.12 (brs, 1H), 6.04 (s, 1H), 5.46 (s, 1H), 3.87 (s, 3H), 2.90 (s, 3H). $^{13}$C NMR (75

MHz, CDCl$_3$): 170.1, 164.0, 150.7, 147.1, 145.9, 145.0, 134.1, 132.3, 127.8, 127.1, 126.9, 121.8, 118.9, 117.4, 113.0, 110.8, 56.1, 26.5. m/z MS (ESI$^+$): 293 (M+H)$^+$.

2-Methoxy-5-(1-(2-methylquinazolin-4-yl)vinyl) aniline I-7

4-Chloroquinazoline (1 mmol) is added to a mixture containing N-tosylhydrazone NH-acetyl (1.5 mmol), t-BuOLi (2.2 mmol), PdCl$_2$(CH$_3$CN)$_2$ (0.1 mmol) and dppf (0.2 mmol) in dioxane (1 mL). The reaction medium is sealed then heated at 90° C. for 2 hours before being returned to room temperature. The suspension obtained is filtered on a Celite column (eluent AcOEt) to separate the inorganic salts. After evaporation of the solvents under vacuum, the residue formed is dissolved in MeOH (1 mL) then KOH (20 mmol) is added and the reaction medium is sealed then stirred at 100° C. for 12 hours. The suspension thus formed is filtered, the organic solvents are evaporated and the residue formed is chromatographed on a silica gel column.
Yellow oil, 27%. TLC: Rf 0.1 (Cyclohexane/EtOAc, 7/3). IR (neat, cm$^{-1}$): 1614, 1567, 1553, 1441, 1330, 1219. $^1$H NMR (300 MHz, CD$_3$COCD$_3$): 7.94-7.84 (m, 3H), 7.52-7.46 (m, 1H), 6.76-6.72 (m, 2H), 6.54 (dd, 1H, J=8.3 Hz, J=2.3 Hz), 5.96 (s, 1H), 5.33 (s, 1H), 4.41 (brs, 2H), 3.81 (s, 3H), 2.79 (s, 3H). $^{13}$C NMR (75 MHz, CD$_3$COCD$_3$): 170.7, 164.6, 152.1, 148.2, 147.1, 138.5, 134.4, 133.1, 128.9, 127.8, 127.3, 122.9, 116.6, 116.1, 113.0, 111.0, 55.8, 26.6. m/z MS (APCI$^+$): 292 (M+H)$^+$.

2-Methyl-4-(1-(naphthalen-2-yl)vinyl)quinazoline I-8

White solid, 36%. M.p.: 113.6° C. TLC: Rf 0.2 (Cyclohexane/EtOAc, 7/3). IR (neat, cm$^{-1}$): 1614, 1568, 1490, 1325, 1168, 906. $^1$H NMR (300 MHz, CDCl$_3$): 8.01 (d, 1H, J=8.4 Hz), 7.86 (d, 1H, J=8.4 Hz), 7.83-7.77 (m, 3H), 7.68-7.65 (m, 1H), 7.60-7.57 (m, 2H), 7.46-7.34 (m, 3H), 6.28 (s, 1H), 5.68 (s, 1H), 2.98 (s, 3H). $^{13}$C NMR (75 MHz, CDCl$_3$): 169.6, 164.1, 151.1, 145.6, 136.1, 134.0, 133.3, 133.1, 128.5, 128.4, 128.0, 127.6, 127.0, 126.8, 126.5, 126.4, 126.4, 124.1, 121.7, 119.3, 26.8. m/z MS (ESI$^+$): 297 (M+H)$^+$.

2-Methyl-4-(1-(1-methyl-1H-indol-5-yl)vinyl)quinazoline I-9

Reddish oil, 46%. TLC: Rf 0.2 (Cyclohexane/EtOAc, 7/3). IR (neat, cm$^{-1}$): 1612, 1565, 1490, 1332, 1246. $^1$H NMR (300 MHz, CDCl$_3$): 8.00 (d, 1H, J=8.4 Hz), 7.91 (dd, 1H, J=8.4 Hz, J=0.7 Hz), 7.83-7.77 (ddd, 1H, J=8.4 Hz, J=6.9 Hz, J=1.4 Hz), 7.50-7.49 (m, 1H), 7.40-7.34 (ddd, 1H, J=8.4 Hz, J=6.7 Hz, J=1.3 Hz), 7.30-7.27 (m, 2H), 7.03 (d, 1H, J=3.1 Hz), 6.41 (d, 1H, J=3.1 Hz), 6.12 (d, 1H, J=0.7 Hz), 5.53 (d, 1H, J=0.7 Hz), 3.77 (s, 3H), 2.99 (s, 3H). $^{13}$C NMR (75 MHz, CDCl$_3$): 170.6, 164.1, 151.0, 146.8, 136.7, 133.7, 130.7, 129.7, 128.6, 127.9, 127.4, 126.6, 121.9, 120.6, 119.7, 116.7, 109.5, 101.7, 33.0, 26.8. m/z MS (APCI$^+$): 300 (M+H)$^+$.

2-Chloro-4-[1-(4-methoxy-phenyl)-vinyl]-quinazoline I-10

Brown oil, 46%. TLC: Rf 0.4 (Cyclohexane/EtOAc, 7/3). IR (neat, cm$^{-1}$): 1673, 1597, 1511, 1246, 1175. $^1$H NMR (300 MHz, CDCl$_3$): 8.0 (dd, 1H, J=8.5 Hz, J=1.1 Hz), 7.90-7.85 (m, 2H), 7.49 (td, 1H, J=8.5 Hz, J=1.1 Hz), 7.23 (d, 2H, J=8.8 Hz), 6.84 (d, 2H, J=8.8 Hz), 6.06 (s, 1H), 5.55 (s, 1H), 3.79 (s, 3H). $^{13}$C NMR (75 MHz, CDCl$_3$): 173.1, 160.1, 157.3, 152.7, 144.2, 135.1, 131.1, 128.1 (2C), 128.1, 127.9, 127.5, 122.4, 118.6, 114.3 (2C), 55.4. m/z MS (APCI$^+$): 297 (M+H)$^+$.

2-Chloro-4-[1-(3,4-dimethoxy-phenyl)-vinyl]-quinazoline I-11

Yellow oil, 19%. TLC: Rf 0.3 (Cyclohexane/EtOAc, 7/3). IR (neat, cm$^{-1}$): 1665, 1595, 1563, 1514, 1465, 1264, 1143. $^1$H NMR (300 MHz, CDCl$_3$): 8.00 (d, 1H, J=8.9 Hz), 7.91-7.85 (m, 2H), 7.49 (td, 1H, J=8.2 Hz, J=1.2 Hz), 6.95 (d, 1H, J=2.0 Hz), 6.77 (d, 1H, J=8.4 Hz), 6.71 (dd, 1H, J=8.3 Hz, J=2.0 Hz), 6.05 (s, 1H), 5.59 (s, 1H), 3.86 (s, 3H), 3.83 (s, 3H). $^{13}$C NMR (75 MHz, CDCl$_3$): 172.8, 157.2, 152.7, 149.7, 149.2, 144.5, 135.2, 131.5, 128.0, 128.0, 127.4, 122.4, 120.2, 119.2, 111.2, 109.6, 56.1, 56.0. m/z MS (APCI$^+$): 327 (M+H)$^+$.

2-Chloro-4-[1-(3,4,5-trimethoxy-phenyl)-vinyl]-quinazoline I-12

White solid, 34%. M.p.: 135-136° C. TLC: Rf 0.4 (Cyclohexane/EtOAc, 7/3). IR (neat, cm$^{-1}$): 1580, 1528, 1401, 1316, 1277, 1243, 1121. $^1$H NMR (300 MHz, CDCl$_3$): 8.01 (d, 1H, J=8.9 Hz), 7.92-7.87 (m, 2H), 7.55-7.49 (m, 1H), 6.52 (s, 2H), 6.09 (s, 1H), 5.66 (s, 1H), 3.85 (s, 3H), 3.66 (s, 6H). $^{13}$C NMR (75 MHz, CDCl$_3$): 172.4, 157.2, 153.5 (2C), 152.7, 144.9, 138.8, 135.3, 134.3, 128.1 (2C), 127.3, 122.3, 120.8, 104.5 (2C), 61.1, 56.4 (2C). m/z MS (ESI$^+$): 357 (M+H)$^+$.

4-[1-(3,5-Dimethoxy-phenyl)-vinyl]-2-methyl-quinazoline I-13

White solid, 36%. F. 89-91° C. Rf 0.3 (Cyclohexane/EtOAc, 7/3). IR (neat, cm$^{-1}$): 1592, 1460, 1424, 1294, 1206, 1161. $^1$H NMR (300 MHz, CDCl$_3$): 7.96 (d, 1H, J=8.4 Hz), 7.87-7.78 (m, 2H), 7.42 (td, 1H, J=8.1 Hz, J=1.0 Hz), 6.45 (d, 2H, J=2.1 Hz), 6.41 (d, 1H, J=2.0 Hz), 6.12 (s, 1H), 5.58 (s, 1H), 3.72 (s, 6H), 2.93 (s, 3H). $^{13}$C NMR (75 MHz, CDCl$_3$); 169.3, 164.1, 161.0 (2C), 151.1, 145.7, 141.0, 134.0, 128.1, 127.0, 126.8, 121.7, 119.5, 105.4 (2C), 100.2, 55.5 (2C), 26.8. m/z MS (APCI$^+$): 307 (M+H)$^+$.

2-Methyl-4-[1-(3,4,5-trimethoxy-phenyl)-vinyl]quinazoline I-14

Yellow solid, 40%. F. 127-128° C. Rf 0.2 (Cyclohexane/EtOAc, 7/3). IR (neat, cm$^{-1}$): 1553, 1506, 1464, 1410, 1331, 1242, 1128. $^1$H NMR (300 MHz, CDCl$_3$): 7.97 (d, 1H, J=8.5 Hz), 7.90-7.80 (m, 2H), 7.45 (td, 1H, J=8.2 Hz, J=1.1 Hz), 6.54 (s, 2H), 6.07 (s, 1H), 5.56 (s, 1H), 3.84 (s, 3H), 3.72 (s, 6H), 2.94 (s, 3H). $^{13}$C NMR (75 MHz, CDCl$_3$): 169.3, 164.1, 153.4 (2C), 151.2, 145.7, 138.6, 134.7, 134.0, 128.1, 127.0, 126.9, 121.7, 119.0, 104.5 (2C), 61.0, 56.3 (2C), 26.8. m/z MS (ESI$^+$): 359 (M+Na)$^+$.

The compound 3-(2-Methoxy-5-(1-(2-methylquinazolin-4-yl)vinyl)phenyl)prop-2-yn-1-ol I-15 was prepared in three steps starting with commercial 3-iodo-4-methoxyacetophenone (Scheme 1). The first step is a Sonogashira reaction to install the acetylenic functional group. The ketone thus formed is transformed into N-tosylhydrazone derivative then the latter is coupled under palladium-catalysed conditions with 4-chloroquinazoline to yield compound I-15.

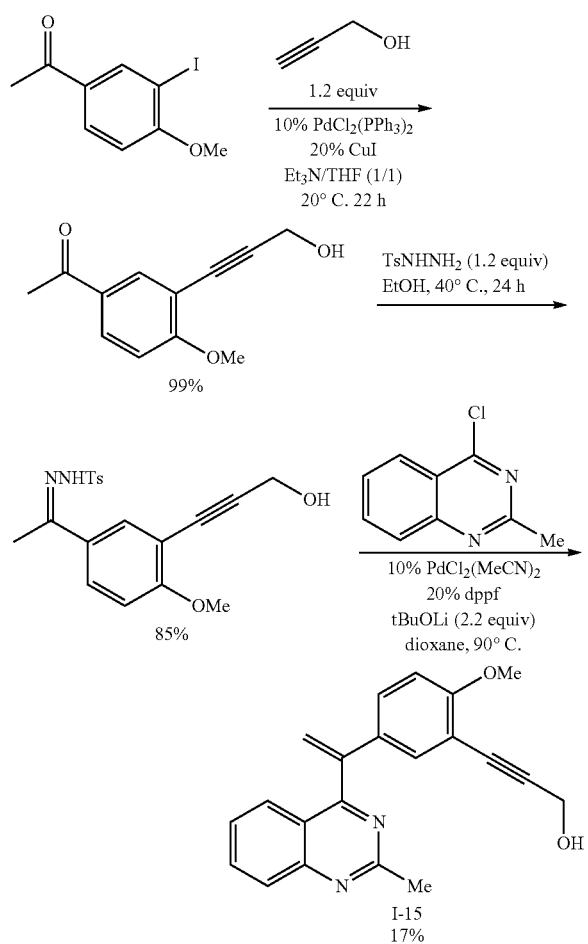

Yellow oil, 17%, TLC: Rf 0.1 (Cyclohexane/EtOAc, 1/1). IR (neat, cm$^{-1}$): 3272, 2927, 2840, 2247, 1777, 1599, 1361, 873. $^1$H NMR (300 MHz, CDCl$_3$): 8.01 (d, 1H, J=8.3 Hz), 7.82 (m, 2H), 7.46, (t, 1H, J=7.5 Hz), 7.41 (s, 1H), 7.22 (d, 1H, J=7.5 Hz), 6.77 (d, 1H, J=8.5 Hz), 6.02 (s, 1H), 5.50 (s, 1H), 4.50 (s, 2H), 3.78 (s, 3H), 2.90 (s, 3H), OH not seen). $^{13}$C NMR (300 MHz, CDCl$_3$): 169.5, 163.9, 160.0, 150.7, 144.1, 134.1, 131.9, 131.2, 128.4, 127.8, 126.9, 126.8, 121.5, 117.9, 112.1, 110.7, 92.0, 81.3, 55.9, 51.6, 26.5. HRMS (ESI$^+$): m/z calculated for C$_{21}$H$_{19}$N$_2$O$_2$ [M+H]$^+$ 331.1447. found 331.1441.

The compound 4-(1-(4-Methoxyphenyl)vinyl)quinoline-2-carbonitrile I-16 is prepared from 2,4-dichloroquinoline by first carrying out a selective cyanation reaction at position C$_2$ (scheme 2). The 2-cyano-4-chloroquinoline thus formed with 83% yield is then coupled with N-tosylhydrazone of 4-methoxyacetophenone.

Yellow oil, 62%, TLC: Rf 0.4 (Cyclohexane/EtOAc, 9/1). R (neat, cm$^{-1}$): 3062, 3004, 2958, 2934, 2838, 2236, 1675, 1605, 1576, 1545, 1511, 1459, 1218, 1153, 1098, 909. $^1$H NMR (300 MHz, CDCl$_3$): 8.20 (d, 1H, J=9.1 Hz), 7.91-7.78 (m, 2H), 7.65 (s, 1H), 7.61-7.50 (m, 1H), 7.18 (d, 2H, J=9.0 Hz), 682 (d, 2H, J=9.0 Hz), 6.01 (s, 1H), 5.36 (s, 1H), 3.79 (s, 3H). $^{13}$C NMR (300 MHz, CDCl$_3$): 160.1, 150.8, 148.7, 144.3, 133.7, 131.7, 131.1, 130.4, 129.4, 127.9 (2C), 126.4, 123.8, 117.7, 116.6, 114.3 (2C), 55.4. HRMS (ESI$^+$): m/z calculated for C$_{19}$H$_{14}$N$_2$O [M+H]$^+$ 287.1184. found 287.1180.

The compound 4-Chloro-2-(1-(4-methoxyphenyl)vinyl)quinoline I-17 is prepared from 2,4-dichloroquinoline Brown oil, 47%, TLC: Rf 0.5 (Cyclohexane/EtOAc, 9/1). IR (neat, cm$^{-1}$): 3400, 3063, 3001, 2956, 2933, 2907, 2836, 1939, 1652, 1607, 1440, 1245, 907, 846. $^1$H NMR (300 MHz, CDCl$_3$): 8.25-8.17 (m, 2H), 7.81-7.75 (td, 1H, J=6.9 Hz, J=1.5 Hz), 7.69-7.61 (td, 1H, J=6.9 Hz, J=1.5 Hz), 7.50 (s, 1H), 7.30 (d, 2H, J=9.0 Hz), 6.89 (d, 2H, J=9.0 Hz), 6.04 (d, 1H, J=1.3 Hz), 5.75 (d, 1H, J=1.3 Hz), 3.79 (s, 3H). $^{13}$C NMR (300 MHz, CDCl$_3$): 159.8, 159.1, 148.5, 147.9, 143.0, 132.0, 130.8, 130.0, 129.7 (2C), 127.6, 125.7, 124.0, 121.4, 118.7, 114.0 (2C), 55.5. HRMS (ESI$^+$): m/z calculated for C$_{18}$H$_{15}$ClNO [M+H]$^+$ 296.0842. found 296.0842.

The compound 1-(1-(4-Methoxyphenyl)vinyl)-3-methylisoquinoline I-18 is prepared from 1-chloro-3-methylisoquinoline) White solid, 40%, F=66° C., TLC: Rf 0.42 (Cyclohexane/EtOAc, 3/7). IR (neat, cm$^{-1}$): 2955, 2835, 1621, 1606, 1589, 1464, 1298, 1285, 1098, 879. $^1$H NMR (300 MHz, CDCl$_3$): 7.82 (d, 1H, J=9.0 Hz), 7.66 (d, 1H, J=9.0 Hz), 7.51 (t, 1H, J=9.0 Hz), 7.40 (s, 1H), 7.27 (t, 1H, J=9.0 Hz), 7.16 (d, 2H, J=9.1 Hz), 6.69 (d, 2H, J=9.1 Hz), 5.94 (s, 1H), 5.31 (s, 1H), 3.69 (s, 3H), 2.65 (s, 3H). $^{13}$C NMR (300 MHz, CDCl$_3$): 160.9, 159.4, 150.9, 146.6, 137.2, 132.5, 130.0, 127.8 (2C), 127.4, 126.2, 126.1, 125.4, 118.2, 115.4, 113.7 (2C), 55.2, 24.5. HRMS (ESI$^+$): m/z calculated for C$_{19}$H$_{18}$NO [M+H]$^+$ 276.1388. found 276.1385.

The compound 4-(1-(4-Methoxyphenyl)vinyl)-2-methylquinoline I-19 is prepared from 4-chloro-2-methylquinoline) White solid, 65%, F=94° C., TLC: Rf 0.24 (Cyclohexane/EtOAc, 8/2). IR (neat, cm$^{-1}$): 2961, 2929, 1734, 1651, 1607, 1560, 1440, 1409, 1378, 1097, 902, 836. $^1$H NMR (300 MHz, CDCl$_3$): 8.04 (d, 1H, J=8.2 Hz), 7.72 (d, 1H, J=8.3 Hz), 7.62 (dd, 1H, J=8.35, J=6.92), 7.22 (t, 1H, J=8.3 Hz), 7.18 (m, 3H), 6.80 (d, 2H, J=8.0 Hz), 5.80 (s, 1H), 5.31 (s, 1H), 3.77 (s, 3H), 2.76 (s, 3H). $^{13}$C NMR (300 MHz, CDCl$_3$): 158.5, 157.7, 147.7, 147.1, 144.5, 131.3, 128.2, 127.8, 126.7 (2C), 125.0, 124.5, 124.4, 121.3, 113.9, 112.8 (2C), 54.2, 24.3. HRMS (ESI$^+$): m/z calculated for C$_{19}$H$_{18}$NO [M+H]$^+$ 276.1388. found 276.1388.

General Procedure for Synthesizing Compounds II-1 to II-4

A solution of 1-quinazoline-1-arylethylenes (I) (1 mmol) in EtOAc (1 mL) is placed under atmospheric pressure of hydrogen in the presence of Pd/C (20% by mass) then stirred for 2 to 5 hours. After filtration on Celite, the solvents are evaporated under vacuum, and the residue formed is chromatographed on a silica gel column.

4-[1-(4-Methoxy-phenyl)-ethyl]-2-methyl-quinazoline II-1

Brown oil, 99%. TLC: Rf 0.4 (Cyclohexane/EtOAc, 7/3). IR (neat, cm$^{-1}$): 2925, 1612, 1564, 1511, 1463, 1247, 1178. $^1$H NMR (300 MHz, CDCl$_3$): 8.07 (d, 1H, J=8.4 Hz), 7.91 (d, 1H, J=8.4 Hz), 7.75-7.69 (m, 1H), 7.45-7.39 (m, 1H), 7.24 (d, 2H, J=8.7 Hz), 6.79 (d, 2H, J=8.7 Hz), 4.95 (q, 1H, J=6.9 Hz), 3.71 (s, 3H), 2.92 (s, 3H), 1.78 (d, 3H, J=6.9 Hz). $^{13}$C NMR (75 MHz, CDCl$_3$): 172.4, 163.8, 158.2, 150.7, 136.5, 133.0, 128.6 (2C), 128.5, 126.4, 124.6, 121.4, 114.1 (2C), 55.2, 42.2, 26.8, 21.3. m/z MS (APCI$^+$): 279 (M+H)$^+$.

4-[1-(3,4-Dimethoxy-phenyl)-ethyl]-2-methyl-quinazoline II-2

Yellow oil, 97%. TLC: Rf 0.2 (Cyclohexane/EtOAc, 7/3). IR (neat, cm$^{-1}$): 1563, 1514, 1491, 1418, 1328, 1262, 1140. $^1$H NMR (300 MHz, CDCl$_3$): 8.10 (d, 1H, J=8.2 Hz), 7.90 (d, 1H, J=8.3 Hz), 7.75 (ddd, 1H, J=8.2 Hz, J=6.9 Hz, J=1.2 Hz), 7.45 (ddd, 1H, J=8.2 Hz, J=6.8 Hz, J=1.1 Hz), 6.92 (d, 1H, J=2.0 Hz), 6.86 (dd, 1H, J=8.2 Hz, J=2.0 Hz), 6.75 (d, 1H, J=8.2 Hz), 4.94 (q, 1H, J=6.9 Hz), 3.82 (s, 3H), 3.81 (s, 3H), 2.91 (s, 3H), 1.78 (d, 3H, J=6.9 Hz). $^{13}$C NMR (75 MHz, CDCl$_3$): 172.3, 163.8, 150.8, 149.1, 147.8, 137.0, 133.2, 128.6, 126.5, 124.7, 121.4, 119.8, 111.3, 111.0, 56.0, 55.9, 42.6, 26.9, 21.4. m/z MS (APCI$^+$): 309 (M+H)$^+$.

2-Methyl-4-[1-(3,4,5-trimethoxy-phenyl)-ethyl]-quinazoline II-3

Yellow oil, 97%. Rf 0.2 (Cyclohexane/EtOAc, 7/3). IR (neat, cm$^{-1}$): 1587, 1564, 1492, 1461, 1420, 1328, 1238, 1122. $^1$H NMR (300 MHz, CDCl$_3$): 8.1 (d, 1H, J=8.2 Hz), 7.91 (d, 1H, J=8.3 Hz), 7.76 (ddd, 1H, J=8.2 Hz, J=7.1 Hz, J=1.3 Hz), 7.47 (ddd, 1H, J=8.2 Hz, J=7.0 Hz, J=1.2 Hz), 6.58 (s, 2H), 4.91 (q, 1H, J=6.9 Hz), 3.79 (s, 6H), 3.77 (s, 3H), 2.91 (s, 3H), 1.78 (d, 3H, J=6.9 Hz). $^{13}$C NMR (75 MHz, CDCl$_3$): 172.0, 163.8, 153.3 (2C), 150.8, 140.0, 136.8, 133.2, 128.6, 126.6, 124.6, 121.5, 105.0 (2C), 60.9, 56.2 (2C), 43.2, 26.8, 21.5. m/z MS (APCI$^+$): 339 (M+H)$^+$.

4-[1-(3,5-Dimethoxy-phenyl)-ethyl]-2-methyl-quinazoline II-4

Brown oil, 89%. Rf 0.3 (Cyclohexane/EtOAc, 7/3). IR (neat, cm$^{-1}$): 1609, 1593, 1564, 1428, 1205, 1157. $^1$H NMR (300 MHz, CDCl$_3$): 8.08 (d, 1H, J=8.2 Hz), 7.90 (d, 1H, J=8.4 Hz), 7.77-7.72 (ddd, 1H, J=8.2 Hz, J=6.9 Hz, J=1.3 Hz), 7.44 (ddd, 1H, J=8.3 Hz, J=7.0 Hz, J=1.0 Hz), 6.49 (d, 2H, J=2.2 Hz), 6.27 (t, 1H, J=2.2 Hz), 4.90 (q, 1H, J=6.9 Hz), 3.73 (s, 6H), 2.91 (s, 3H), 1.78 (d, 3H, J=6.9 Hz). $^{13}$C NMR (75 MHz, CDCl$_3$): 171.8, 163.8, 161.0 (2C), 150.7, 146.9, 133.2, 128.5, 126.6, 124.7, 121.6, 106.2 (2C), 98.0, 55.4 (2C), 43.4, 26.9, 21.1. m/z MS (APCI$^+$): 309 (M+H)$^+$.

Cytotoxicity Protocol.

U87, H1299 and MDA-MB231 cells are grown in Dulbecco minimal essential medium (DMEM) containing 4.5 g/L glucose and supplemented with 10% foetal calf serum and 1% glutamine. K562 and HCT116 cells are grown in RPMI 1640 medium containing 10% foetal calf serum and 1% glutamine. All the cell lines are maintained in culture at 37° C. in a humid atmosphere containing 5% CO$_2$. The cells are inoculated in 96-well culture plates in an amount of 5000 cells per well in 50 μL of culture medium. After 24 hours of culture, the molecule to be tested, dissolved in DMSO and diluted 1/1000 in suitable culture medium, is added in each well in an amount of 50 μL per well. After 72 hours of incubation, 20 μL of resazurin is added in each well. After 1 hour of incubation, emitted fluorescence is measured at 590 nm after excitation at 560 nm using the Victor fluorescence reader (Perkin-Elmer, USA). Each concentration is tested three times and each experiment is repeated three times.

Protocol for Inhibition of Polymerisation of Tubulin.

When tubulin is placed at a temperature of 0° C., it is in the form of free dimers. On the other hand, when the temperature is suddenly increased to 37° C., the dimers assemble into microtubules. The IPT of the various synthesized analogues was determined on a soluble tubulin according to the method of Shelanski[7] from sheep brains where it constitutes 20 to 25% of soluble proteins. The "antitubulin" activity is evaluated according to the method of Gaskin[8] by measuring turbidity, which is proportional to the microtubule concentration in the suspension. Turbidity is measured by absorption of the suspension at 350 nm using a spectrophotometer fitted with a cell thermostatically-controlled at 37° C. The various samples were dissolved in DMSO and incubated 10 minutes at 37° C. then 5 minutes at 0° C.

The tubulin assembly and disassembly curves are obtained by absorption kinetics at 350 nm as a function of time. The IC$_{50}$ determined graphically is defined as the concentration of inhibitor necessary to decrease by 50% the maximum rate of assembly of the control tubulin.

In Vitro Biological Study of Compounds of the Present Invention

Their effects on the proliferation of various human cancer cell lines and their capacity to inhibit the polymerisation of tubulin were tested.

A. Cytotoxic Activity

The cytotoxic activity of the compounds was studied in vitro principally on the HCT116 human cancer cell line (colorectal cancer). The line selected for this study was incubated at 37° C. in the presence of one of the compounds added in the culture medium at various concentrations. The inhibitory concentration inducing the death of 50% of the cells (IC$_{50}$) was determined after 72 hours of incubation (Table 1) for each compound. The set of experiments carried out made it possible to determine the degree of toxicity of the compounds tested by taking isoCA-4 as the reference. In view of the results, it appears that several compounds have IC$_{50}$ values at a nanomolar level and that compounds I-5, I-6, I-7, I-15, I-16, I-19 are the most cytotoxic with IC$_{50}$ values below 20 nM. It should be noted that the first structure-activity relationships are in perfect agreement with the previous results observed in the isoCA-4 and isoerianin series, namely that the most effective B rings are substituted at C-4 with a OMe group and at C-3 by a fluorine atom (I-5), a OH (I-6) or NH$_2$ (I-7) group. Moreover, by comparing the results obtained with the cytotoxic compounds I-1 and I-10, it appears that the quinazoline nucleus may be substituted at C-2 with a methyl group or a chlorine atom with no loss of efficacy (I-1 and I-10: IC$_{50}$=40 nM). Lastly, when these first results are examined, it appears that the reduction of the double bond located between the two aromatic nuclei yields "reduced" type II derivatives about 10 times less cytotoxic than their precursors I as we had already noted during the reduction of isoCA-4 derivatives to isoerianin-type derivatives. Molecule I-15 shows that the introduction of an acetylenic carbon-containing substituent at C3' considerably improves the cytotoxic activity compared to I-1. In addition, replacing the quinazoline nuclei with other heterocycles made it possible to identify molecules exhibiting better cytotoxic activities at sub-nanomolar concentrations.

TABLE 1

Cytotoxicity results of the compounds on the HCT116 human cancer cell line (colorectal cancer). Cytotoxic activity (IC$_{50}$) is expressed in nMol/L and corresponds to the concentration of the compounds which induces 50% cell death after 72 hours of incubation.

| Compounds | | HCT116 IC$_{50}$ (nM) |
|---|---|---|
| 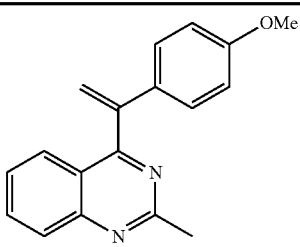 | I-1 | 38 |

TABLE 1-continued
Cytotoxicity results of the compounds on the HCT116 human cancer cell line (colorectal cancer). Cytotoxic activity (IC$_{50}$) is expressed in nMol/L and corresponds to the concentration of the compounds which induces 50% cell death after 72 hours of incubation.
| Compounds | | HCT116 IC$_{50}$ (nM) |
|---|---|---|
| 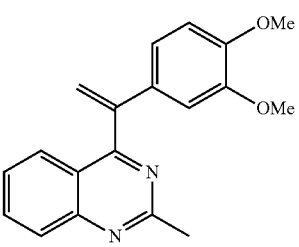 | I-2 | 460 |
| 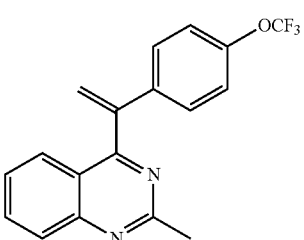 | I-3 | 2300 |
| 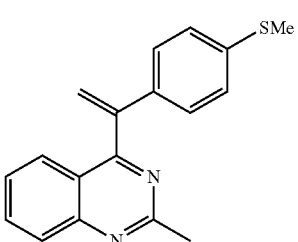 | I-4 | 52 |
| 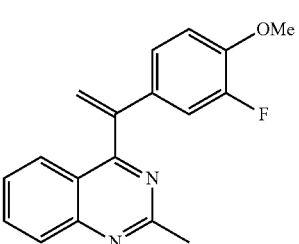 | I-5 | 18 |
| 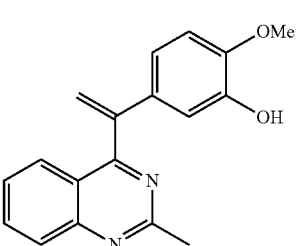 | I-6 | 10 |
| 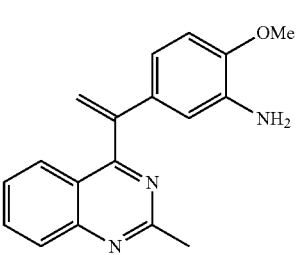 | I-7 | 10 |
| 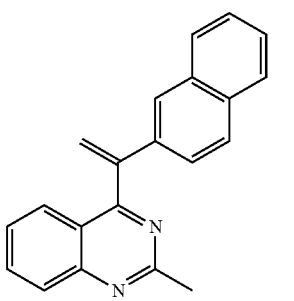 | I-8 | 130 |
| 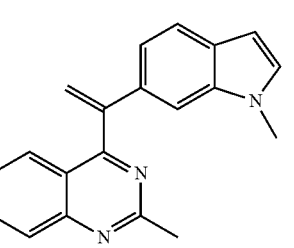 | I-9 | 27 |
| 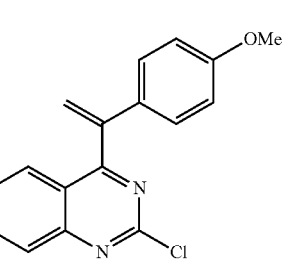 | I-10 | 34 |
| 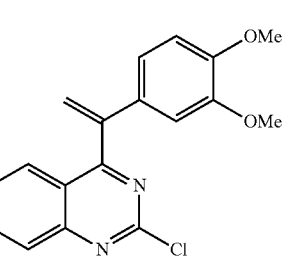 | I-11 | 700 |
| 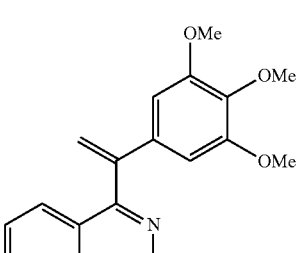 | I-12 | 900 |

TABLE 1-continued

Cytotoxicity results of the compounds on the HCT116 human cancer cell line (colorectal cancer). Cytotoxic activity (IC$_{50}$) is expressed in nMol/L and corresponds to the concentration of the compounds which induces 50% cell death after 72 hours of incubation.

| Compounds | | HCT116 IC$_{50}$ (nM) |
|---|---|---|
| [Structure: 2-methyl-4-(1-(4-methoxyphenyl)ethyl)quinazoline] | II.1 | 250 |
| [Structure: 2-methyl-4-(1-(3,4-dimethoxyphenyl)ethyl)quinazoline] | II-2 | 950 |
| [Structure: quinazoline with vinyl-linked 4-methoxy-2-(propynol)phenyl, 2-Me] | I-15 | 1,5 |
| [Structure: 2-CN-quinoline with vinyl-4-methoxyphenyl] | I-16 | 1,6 |
| [Structure: 4-Cl-quinoline with vinyl-4-methoxyphenyl at C2] | I-17 | 95 |
| [Structure: 3-Me-isoquinoline with vinyl-4-methoxyphenyl] | I-18 | 87 |
| [Structure: 2-Me-quinoline with vinyl-4-methoxyphenyl] | I-19 | ≤1 |
| isoCA-4 | | 2 |

Compounds I-1 and I-10 bearing a methyl substituent and a chlorine atom at C-2 and which had equivalent levels of cytotoxicity (IC$_{50}$=40 nM) with respect to the HCT116 cell line were also evaluated on a K562 chronic myeloid leukaemia line and a H1299 non-small-cell lung cancer line. Compounds I-15, I-16 and I-19 were also evaluated on a K562 chronic myeloid leukaemia line and a K562R imatinib-resistant chronic myeloid leukaemia line. The first cytotoxicity results are reported in Table 2 below.

TABLE 2

Cytotoxicity results of compounds I-1 and I-10 on three human cancer cell lines HCT116 (colorectal cancer), K562 (chronic myeloid leukaemia) and H1299 (non-small-cell lung cancer). Cytotoxic activity (IC$_{50}$) is expressed in nMol/L and corresponds to the concentration of the compounds which induces 50% cell death after 72 hours of incubation.

| Compounds | HCT116 IC$_{50}$ (nM) | K562 IC$_{50}$ (nM) | K562R IC$_{50}$ (nM) | H1299 IC$_{50}$ (nM) |
|---|---|---|---|---|
| I-1 | 38 | 34 | n/a | 22 |
| I-10 | 34 | 38 | n/a | 25 |
| I-15 | 1.5 | 8 | ≤1 | n/a |
| I-16 | 1.6 | 9 | ≤1 | n/a |
| I-19 | ≤1 | 17 | 0.7 | n/a |
| isoCA-4 | 2 | 4 | | 5 |

The results indicate that the cytotoxicity of I-1 and I-10 with respect to the K562 and H1299 lines is similar to that observed with the HCT116 line (IC$_{50}$ between 22 and 38 nM).

Replacing the quinazoline nucleus (I-1) with a quinoline nucleus yielded compound 1-19 having sub-nanomolar cytotoxic activities. It should be noted that replacing the C2 methyl group of compound 1-19 with a cyano group (1-16) has no effect on cytotoxic activity.

B. Inhibition of Polymerisation of Tubulin

The most cytotoxic compounds were selected for tests of inhibition of polymerisation of tubulin. These tests were carried out under the direction of Dr J. Dubois at Gif-sur-Yvette, France. Tubulin is purified from ewe brains according to the method of Shelanski[9] by two assembly-disassembly cycles. The stock solution (15-20 mg/mL), stored at −196° C., is thawed and diluted in assembly buffer (0.1 M MES, 0.5 mM MgCl$_2$, 1 mM EGTA, and 1 mM GTP, pH 6.6) to have a final concentration of 10 μM. Tubulin assembly is monitored by fluorescence on 96-well plates according to the method of Barron et al.[10] Inhibitor (DMSO, 1 μL) is added to the tubulin solution (10 μM, 100 μL per well) and the solution is incubated 45 minutes at room temperature. GTP (1 mM final) is then added, the solution is mixed rapidly and fluorescence ($\lambda_{ex}$=350 nm, $\lambda_{em}$=440 nm) is measured on a Wallac Victor fluorometer (Perkin Elmer). The inhibition of 50% of the maximum rate of assembly ($IC_{50}$) is determined in duplicate or triplicate on 10 concentrations bracketing the $IC_{50}$. The results are recorded in Table 3.

TABLE 3

Results of the inhibition of the polymerisation of tubulin (IPT) by the selected compounds I

| Compounds | | IPT ($IC_{50}$) μM |
|---|---|---|
| 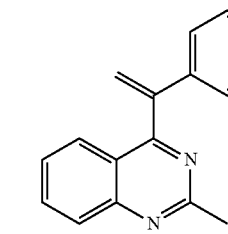 | I-1 | 1.8 |
| | I-4 | 2.9 |
| | I-5 | 1.0 |
| | I-6 | 0.6 |
| | I-7 | 2.3 |

TABLE 3-continued

Results of the inhibition of the polymerisation of tubulin (IPT) by the selected compounds I

| Compounds | | IPT ($IC_{50}$) μM |
|---|---|---|
| 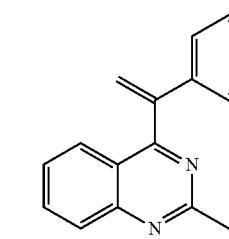 | I-8 | 2.2 |
| | I-9 | 1.6 |
| | I-10 | 1.9 |
| | I-15 | 1.2 |
| | I-16 | 0.96 |

TABLE 3-continued

Results of the inhibition of the polymerisation of tubulin (IPT) by the selected compounds I

| Compounds | | IPT ($IC_{50}$) µM |
|---|---|---|
| 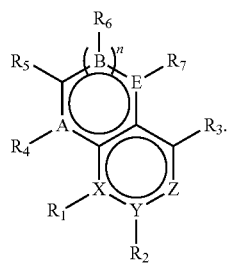 | I-19 | 1.09 |
| isoCA-4 | | 1.0 |
| CA-4 | | 1.0 |

It may be noted that all of the selected compounds inhibit the polymerisation of tubulin at micromolar concentrations (0.6 µM<$IC_{50}$<2.9 µM). In particular, compound I-6, which proved to be very cytotoxic with respect to the HCT116 line, inhibits the assembly of tubulin with a sub-micromolar $IC_{50}$ ($IC_{50}$=0.6 µM).

Molecule I-15 shows that the introduction of an acetylenic carbon-containing substituent at C3' considerably improves the ITP activity compared to I-1. In addition, replacing the quinazoline nucleus with other heterocycles made it possible to identify molecules exhibiting a capacity to inhibit the polymerisation of tubulin at sub-micromolar concentrations.

REFERENCES

1. G. R. Pettit et al *J. Nat. Prod.* 1987, 50, 119.
2. Mc Gown et al *Cancer Chemother. Pharmacol.* 1990, 26, 79.
3. G. G. Dark et al *Cancer Res.* 1997, 57, 1829.
4. (a) S. Messaoudi et al *J. Med. Chem.* 2009, 52, 4538. (b) M. Alami et al WO 2008/122620 (c) A. Hamze et al *ChemMedChem.* 2009, 4, 1912.
5. M. Soussi et al *ChemMedChem,* 2011, 6, 1781.
6. M. Alami et al WO 2009/147217.
7. Shelanski, M. C.; Gaskin, F.; Cantor, C. R. *Proc. Natl. Acad. Sci.* USA, 1973, 70, 765-768.
8. Gaskin, F.; Cantor, C. R.; Shelanski, M. C. *J. Biol. Mol.,* 1974, 89, 737-755.
9. Shelanski, M. L.; Gaskin, F.; Cantor, C. R. *Proc. Natl. Acad. Sci.* USA, 1973, 70, 765-768.
10. Barron, D. M.; Chatterjee, S. K.; Ravindra, R.; Roof, R.; Baloglu, E.; Kingston, D. G. I.; Bane, S. *Anal. Biochem.* 2003, 315 49-56.

The invention claimed is:

1. A compound of formula (I'):

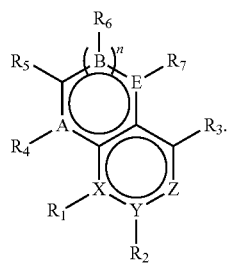

(I')

wherein:
$R_2$ and $R_3$ are different and one of $R_2$ and $R_3$ is a group A1 of the following formula:

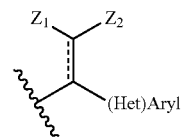

wherein:
the dashed bond is present;
$Z_1$ and $Z_2$ are, independently of each other, a hydrogen atom, a halogen atom or a methyl group;
(Het)Aryl is an aryl or heteroaryl group, said heteroaryl being selected from indolyl, benzothiophenyl and benzofuranyl groups, wherein said aryl or heteroaryl may be substituted with one or more substituents selected from a halogen atom, a hydroxyl group, —OMe, —SMe, —$OCX_3$ with X indicating a halogen atom, —$NH_2$,

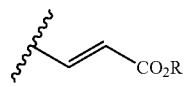

wherein R is a $C_1$-$C_6$ alkyl group,

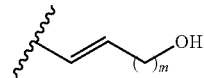

wherein m is 1 or 2,

wherein m is 1 or 2, and

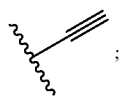

;

and
the other of $R_2$ and $R_3$ is:
a hydrogen atom;
a halogen atom;
a hydroxyl group;
a cyano group;
a —COYR' group wherein Y is O or N and R' is H or a $C_1$-$C_6$ alkyl group, a $C_2$-$C_4$ alkenyl group, or a $C_2$-$C_4$ alkynyl group;
a —$SO_2$NR'R" group wherein R', R" each is, independently of each other, H or a $C_1$-$C_6$ alkyl group, a $C_2$-$C_4$ alkenyl group, or a $C_2$-$C_4$ alkynyl group;
a —$NHSO_2$R' group wherein R' is a $C_1$-$C_6$ alkyl group, a $C_2$-$C_4$ alkenyl group, a $C_2$-$C_4$ alkynyl group, an aryl group, or a heteroaryl group;

a $C_1$-$C_6$ alkyl group;
a $C_2$-$C_4$ alkenyl group;
a $C_2$-$C_4$ alkynyl group;
a $C_1$-$C_6$ alkoxy group; or
a —NR'R" group wherein R' and R" are, independently of each other, a hydrogen or an alkyl group;

A, B and E are, independently of each other, a carbon or nitrogen atom, n is 0 or 1 and $R_4$, $R_5$, $R_6$, $R_7$ are as described below;

X, Y and Z are, independently of each other, a carbon or nitrogen atom provided that if X and Z are a nitrogen atom, Y is a carbon atom;

at least one of A, B, E, X, Y and Z is a nitrogen atom;

$R_1$, $R_4$, $R_5$, $R_6$, $R_7$, if present, are, independently of each other:
a hydrogen atom;
a halogen atom;
a hydroxyl group;
a $C_1$-$C_6$ alkyl group;
a $C_2$-$C_4$ alkenyl group;
a $C_2$-$C_4$ alkynyl group;
a $C_1$-$C_6$ alkoxy group; or
a —NR'R" group wherein R' and R" are, independently of each other, a hydrogen or a $C_1$-$C_6$ alkyl group;

as well as pharmaceutically acceptable salts, and stereoisomers thereof.

2. The compound according to claim 1 having the following formula (Ib):
wherein:

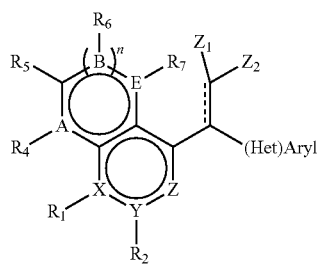

(Ib)

the dashed bond is present;
$R_2$ is:
a hydrogen atom;
a halogen atom;
a hydroxyl group;
a cyano group;
a —COYR' group wherein Y is O or N and R' is H or a $C_1$-$C_6$ alkyl group, a $C_2$-$C_4$ alkenyl group, or a $C_2$-$C_4$ alkynyl group;
a —SO$_2$NR'R" group wherein R', R" are each, independently of each other, H or a $C_1$-$C_6$ alkyl group, a $C_2$-$C_4$ alkenyl group, or a $C_2$-$C_4$ alkynyl group;
a —NHSO$_2$R' group wherein R' is a $C_1$-$C_6$ alkyl group, a $C_2$-$C_4$ alkenyl group, a $C_2$-$C_4$ alkynyl group, an aryl group, or a heteroaryl group;
a $C_1$-$C_6$ alkyl group;
a $C_2$-$C_4$ alkenyl group;
a $C_2$-$C_4$ alkynyl group;
a $C_1$-$C_6$ alkoxy group; or
a —NR'R" group wherein R' and R" are, independently of each other, a hydrogen or an alkyl group;
$Z_1$ and $Z_2$ are, independently of each other, a hydrogen atom, a halogen atom or a methyl group;

(Het)Aryl is an aryl or heteroaryl group, said heteroaryl being selected from indolyl, benzothiophenyl and benzofuranyl groups, wherein said aryl or heteroaryl may be substituted with one or more substituents selected from a halogen atom, a hydroxyl group, —OMe, —SMe, —OCX$_3$ with X indicating a halogen atom, —NH$_2$,

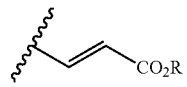

wherein R is a $C_1$-$C_6$ alkyl group,

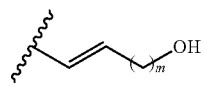

wherein m is 1 or 2,

wherein m is 1 or 2 or

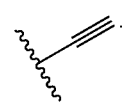

3. The compound according to claim 1 wherein (Het)Aryl is a phenyl group which may be substituted with one or more substituents selected from a halogen atom, a hydroxyl group, —OMe, —SMe, —OCX$_3$ with X indicating a halogen atom, —NH$_2$,

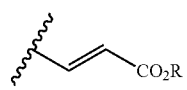

wherein R is a $C_1$-$C_6$ alkyl group,

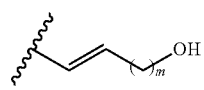

wherein m is 1 or 2,

wherein m is 1 or 2 or

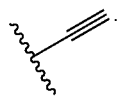

4. The compound according to claim 3 wherein the phenyl group has the following formula:
wherein:

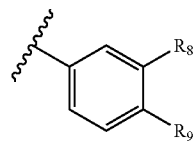

$R_8$ is a hydrogen atom, a halogen atom, a hydroxyl, —OMe, —SMe, —$NH_2$,

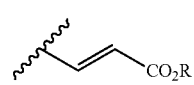

wherein R is a $C_1$-$C_6$ alkyl group,

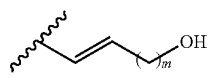

wherein m is 1 or 2,

wherein m is 1 or 2 or

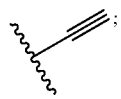

and $R_9$ is a $C_1$-$C_6$ alkoxy group, —SMe or —$OCX_3$ wherein X is a halogen atom.

5. The compound according to claim 1 wherein $Z_1$ and $Z_2$ are a hydrogen atom.

6. The compound according to claim 1 wherein $Z_1$ and $Z_2$ are a fluorine atom.

7. The compound according to claim 1 wherein n is equal to 1, X and Z are a nitrogen atom, A and E are, independently of each other, a nitrogen or carbon atom and Y and B are a carbon atom.

8. The compound according to claim 1, wherein the compound is selected from:

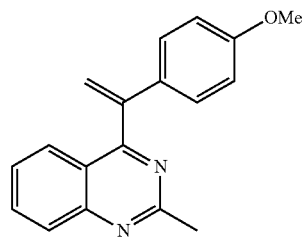 [SMILES: C=C(c1ccc(OC)cc1)c1nc(C)nc2ccccc12]

I-1

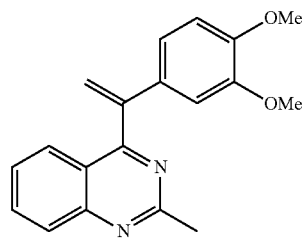

I-2

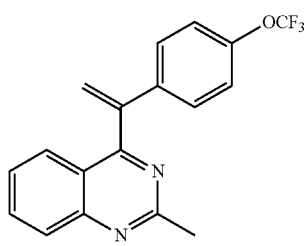

I-3

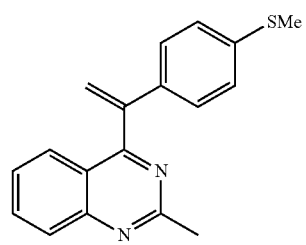 [SMILES: C=C(c1ccc(SC)cc1)c1nc(C)nc2ccccc12]

I-4

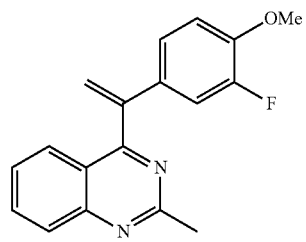 [SMILES: C=C(c1ccc(OC)c(F)c1)c1nc(C)nc2ccccc12]

I-5

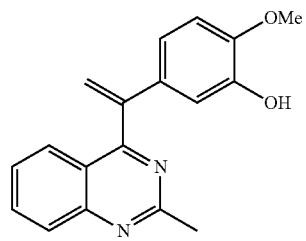 [SMILES: C=C(c1ccc(OC)c(O)c1)c1nc(C)nc2ccccc12]

I-6

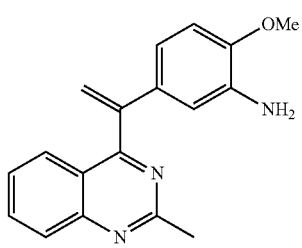 [SMILES: C=C(c1ccc(OC)c(N)c1)c1nc(C)nc2ccccc12]
I-7

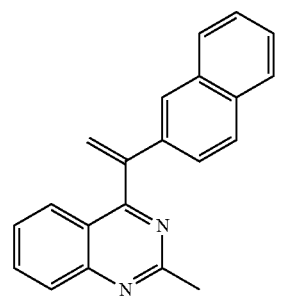 [SMILES: C=C(c1ccc2ccccc2c1)c1nc(C)nc2ccccc12]
I-8

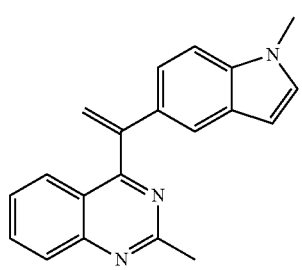
I-9

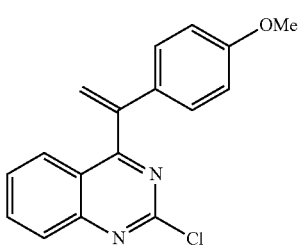 [SMILES: C=C(c1ccc(OC)cc1)c1nc(Cl)nc2ccccc12]
I-10

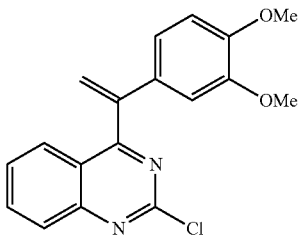
I-11

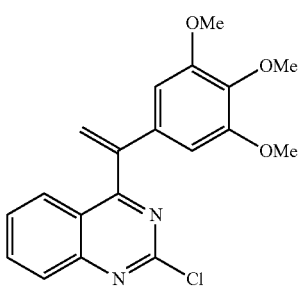
I-12

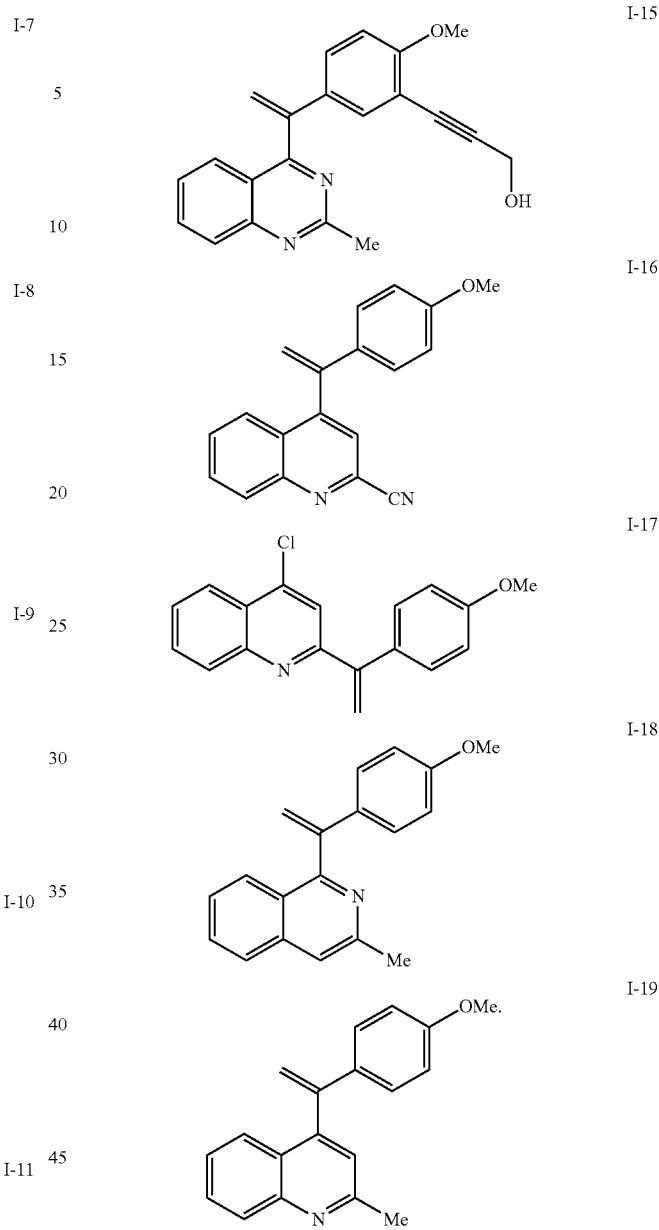

9. A method for treating lung cancer, chronic myeloid leukemia or colorectal cancer, comprising administering to a person in need thereof an effective amount of a compound according to claim 1.

10. A conjugate comprising a compound according to claim 1 bound covalently to an antibody.

11. A pharmaceutical composition comprising a compound according to claim 1.

12. A pharmaceutical composition comprising a conjugate according to claim 10.

13. The pharmaceutical composition according to claim 11 further comprising at least one other active ingredient.

14. The pharmaceutical composition according to claim 13 wherein the other active ingredient is selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

15. A pharmaceutical composition comprising:
   (i) at least one compound of formula (I') according to claim 1 and
   (ii) at least one other active ingredient,
   as a combination product for simultaneous, separate or sequential use.

16. A method for preparing a compound of formula (I') comprising the following successive steps:
   a) reaction of a compound of formula (II)

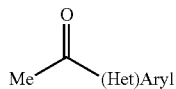
(II)

with tosylhydrazine to yield the tosylhydrazone compound of formula (III)

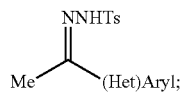
(III)

b) coupling of the compound of formula (III) with the compound of formula (IV), (V), (VI) or (VII)

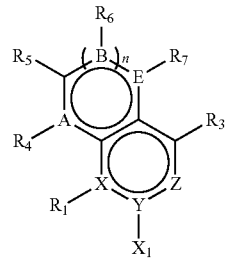
(IV)

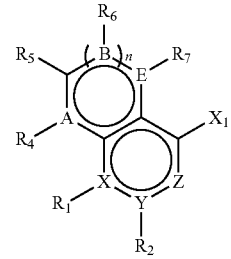
(V)

wherein $R_1$, $R_2$, $R_3$, $R_4$, $R_5$, $R_6$, $R_7$, X, Y, Z, A, B, E and n are as defined in claim 1 and $X_1$ represents a halogen atom or trifluoromethanesulfonate;

c) separation from the reaction medium of compound (I') obtained following the previous step.

* * * * *